(12) United States Patent
Bois et al.

(10) Patent No.: US 9,664,648 B2
(45) Date of Patent: May 30, 2017

(54) METHOD FOR CHARACTERISING THE MECHANICAL BEHAVIOUR OF CEMENTS

(71) Applicant: Total SA, Courbevoie (FR)

(72) Inventors: Axel-Pierre Bois, Curis-au-Mont-d'Or (FR); Andre Garnier, Montardon (FR); Jean-Benoit Laudet, Pau (FR); Manh-Huyen Vu, Noisel (FR); Siavash Ghabezloo, Paris (FR); Jean Sulem, Paris (FR)

(73) Assignee: Total SA, Courbevoie (FR)

(*) Notice: Subject to any disclaimer, the term of this patent is extended or adjusted under 35 U.S.C. 154(b) by 359 days.

(21) Appl. No.: 14/379,549

(22) PCT Filed: Feb. 21, 2013

(86) PCT No.: PCT/FR2013/050355
§ 371 (c)(1),
(2) Date: Aug. 19, 2014

(87) PCT Pub. No.: WO2013/124588
PCT Pub. Date: Aug. 29, 2013

(65) Prior Publication Data
US 2015/0033862 A1   Feb. 5, 2015

(30) Foreign Application Priority Data
Feb. 22, 2012   (FR) .................... 12 51612

(51) Int. Cl.
*G01N 29/024* (2006.01)
*G01N 29/07* (2006.01)
*G01N 33/38* (2006.01)

(52) U.S. Cl.
CPC ........... *G01N 29/024* (2013.01); *G01N 29/07* (2013.01); *G01N 33/383* (2013.01);
(Continued)

(58) Field of Classification Search
CPC ......... G01N 2291/0421; G01N 29/024; G01N 29/02; G01N 29/07; G01N 33/383;
(Continued)

(56) References Cited

U.S. PATENT DOCUMENTS

| 2,538,114 A | 1/1951 | Mason |
| 3,401,773 A | 9/1968 | Synnott, III |

(Continued)

FOREIGN PATENT DOCUMENTS

| EP | 1541987 | 6/2005 |
| WO | 2007/020435 | 2/2007 |

OTHER PUBLICATIONS

Bernard et al., "A multiscale micromechanics-hydration model for the early-age elastic properties of cement-based materials," Cement and Concrete Research, 33:1293-1309 (2003).
(Continued)

*Primary Examiner* — Paul West
*Assistant Examiner* — Xin Zhong
(74) *Attorney, Agent, or Firm* — McAndrews, Held and Malloy

(57) ABSTRACT

The present invention relates to a method for determining mechanical parameters of a cementitious system, on the basis of time, and on the basis of the fineness of the cementitious system, pressure and/or temperature, representative of the in situ conditions found in wellbores. The initial composition of the cementitious system, the fineness $\Phi$ thereof and the speed of the compression waves on the basis of time $V_p(t)$ are the only input data of the method. Said method comprises: ∎ a step A of estimating the degree of hydration of the cementitious system on the basis of time $\alpha(t)$ from $V_p(t)$, at a pressure P1 and a temperature T1; ∎ a step B wherein $\alpha(t)$ is determined on the basis of desired values of fineness $\Phi n$ of the cementitious system, pressure
(Continued)

Pn and/or temperature Tn; ■ a step C wherein the composition of the cementitious system is determined on the basis of time C(t) and on the basis of desired values of fineness Φn of the cementitious system, pressure Pn and/or temperature Tn from α(t) determined in step B; ■ and a step D of determining at least one mechanical parameter of the cementitious system on the basis of time and on the basis of desired values of fineness Φn of the cementitious system, pressure Pn and/or temperature Tn, from C(t) determined in step C. According to the method of the invention, these parameters can be determined while the cementitious system is still very young. In particular, the parameters of static deformability and hydro-mechanical coupling parameters are determined by the method according to the invention.

20 Claims, 8 Drawing Sheets

(52) U.S. Cl.
CPC .. *G01N 2291/011* (2013.01); *G01N 2291/022* (2013.01); *G01N 2291/0232* (2013.01); *G01N 2291/0251* (2013.01); *G01N 2291/02441* (2013.01); *G01N 2291/02827* (2013.01)

(58) Field of Classification Search
CPC ..... G01N 2291/0232; G01N 2291/022; G01N 2291/0251; G01N 2291/02827; G01N 2291/011; G01N 2291/02441
See application file for complete search history.

(56) References Cited

U.S. PATENT DOCUMENTS

| | | | |
|---|---|---|---|
| 4,255,798 A | 3/1981 | Havira | |
| 4,259,868 A | 4/1981 | Rao et al. | |
| 4,779,236 A | 10/1988 | Sondergeld | |
| 4,813,028 A | 3/1989 | Liu | |
| 5,001,676 A | 3/1991 | Broding | |
| 5,168,470 A | 12/1992 | Dennis et al. | |
| 5,357,481 A | 10/1994 | Lester et al. | |
| 5,412,990 A | 5/1995 | D'Angelo et al. | |
| 5,763,773 A | 6/1998 | Birchak et al. | |
| 5,859,811 A | 1/1999 | Miller et al. | |
| 6,941,819 B1 * | 9/2005 | Maki, Jr. ................ | G01N 29/07 73/788 |
| 7,089,816 B2 | 8/2006 | Hakimuddin | |
| 7,549,320 B2 | 6/2009 | Funkhouser et al. | |
| 7,552,648 B2 | 6/2009 | McMechan et al. | |
| 7,621,186 B2 | 11/2009 | Heathman et al. | |
| 2002/0112540 A1 * | 8/2002 | Zeroug ................... | G01N 29/07 73/579 |
| 2013/0192382 A1 * | 8/2013 | Bois ..................... | G01N 33/383 73/803 |

OTHER PUBLICATIONS

Boumiz et al., "Mechanical properties of cement pastes and mortars at early ages," Adv Cem Bas Mat, 3:94-106 (1996).

Ghabezloo, "Association of macroscopic laboratory testing and micromechanics modelling for the evaluation of the poroelastic parameters of a hardened cement paste," Cement and Concrete Research, 40:1197-1210 (2010).

Haecker et al., "Modeling the linear elastic properties of Portland cement paste," Cement and Concrete Research, 35:1948-1960 (2005).

Jennings, "A model for the microstructure of calcium silicate hydrate in cement paste," Cement and Concrete Research, 30:101-116 (2000).

Jennings, "Colloid model of C-S-H and implications to the problem of creep and shrinkage," Materials and Structures/Concrete Science and Engineering, 37:59-70 (2004).

Jennings, "Refinements to colloid model of C-S-H in cement: CM-II," Cement and Concrete Research, 38:275-289 (2008).

Reddy et al., "Cement mechanical property measurements under wellbore conditions," SPE 95921 (2005).

Ulm et al., "Is concrete a poromechanics material?—A multiscale investigation of poroelastic properties," Materials and Structures, 37(265):43-58 (2004).

International Search Report and Written Opinion in PCT/FR2013/050355 dated Jun. 4, 2013.

* cited by examiner

METHOD FOR CHARACTERISING THE MECHANICAL BEHAVIOUR OF CEMENTS

The present application is filed pursuant to 35 U.S.C. 371 as a U.S. National Phase application of International Patent Application No. PCT/FR2013/050355, which was filed Feb. 21, 2013, claiming the benefit of priority to French Patent Application No. 1251612, which was filed on Feb. 22, 2012. The entire text of the aforementioned applications is incorporated herein by reference in its entirety.

FIELD OF THE INVENTION

The field of the invention is characterization of the mechanical behavior of cements, in particular cements used in the operations of wellbore cementing, for example in the context of exploration and production of hydrocarbons. In particular, the invention relates to a method for determining mechanical parameters of a cement system of a given composition, as a function of time, and as a function of the fineness of the cement system, the pressure and/or the temperature.

PRIOR ART

Cementing of an oilwell casing consists of placing a cement sheath in the annular space between the extrados of the casing and the wall of the hole, moreover the hole may consist of another casing or of rock. A cement plug may also be created in the well within the context of drilling or completion operations, or at the moment of final plugging of the latter. This cement sheath or plug has a crucial role in the stability and isolation of oilwells.

The cement sheath or plug is obtained by pumping a cement slurry or grout made from cement, water and admixtures. This cement slurry is in the liquid state when it is pumped. Hydration of the cement particles transforms the liquid slurry to a solid state, characterized by the presence of a skeleton and pores, thus forming a porous medium.

The cement sheath is exposed, during the life of the well and over its entire length, to various mechanical and thermal stresses (in-situ conditions) originating from operations carried out at the surface and in the well (pressure testing, changing of mud, cold and hot stimulation, production of reserves, etc.) or from phenomena arising directly in the subsoil (compaction of the reservoir, earthquakes, etc.), until it is abandoned, or even after that. The cement plug is also subject to various mechanical and thermal stresses. These stresses may damage the material forming the cement sheath or plug, degrade its mechanical and hydraulic properties, and consequently modify its contribution to the stability and imperviousness of the well.

Knowledge of the mechanical behavior of the cement in the in-situ conditions and of the evolution of this behavior over time is essential for analyzing the operation of the well during its drilling, exploitation, and final plugging. For example, it is important to know the mechanical behavior of the cement to guarantee imperviousness of the well during these operations, during storage and sequestration of fluids in underground reservoirs, such as greenhouse gases, e.g. $CO_2$. This knowledge of the mechanical behavior of the cement and of its evolution over time notably makes it possible to simulate, by means of models employing numerical analysis, the service life of the cement sheaths or plugs. The in-situ conditions have an influence on the process of formation of the hardened cement, and consequently on its mechanical behavior. The cements obtained by hardening of slurries in the very specific conditions encountered in wells are in general very different from the cements of the same type formed in ambient conditions (i.e. in the ambient air and at atmospheric pressure). In extreme cases, for wells 6500 meters deep, drilled with muds with a density equal to about 2, the bottomhole pressure may reach more than 130 MPa and the temperature more than 250° C.

There is therefore a need to know the physical and mechanical parameters of the cement and their evolution over time, in different conditions of pressure and temperature, similar to those encountered along the well, and more particularly in the places with the highest pressure and/or temperature stresses. It is interesting in this connection to evaluate these parameters after placement of the cement sheath or plug, i.e. from the youngest age of the cement when hydration of the cement begins to form a structure, also called skeleton, and up to an infinite time corresponding to a fully hydrated cement, in which the hydration processes have ended (stabilization of the composition of the cement, notably of the amount of hydrates).

Numerous techniques for measurement on cement specimens have been proposed for characterizing the mechanical behavior of such materials. The principal mechanical parameters determined from these measurements are the rupture parameters, such as the compressive strength or tensile strength (uniaxial or triaxial), and parameters of deformability, especially elastic parameters of the material such as Young's modulus or Poisson's ratio.

A first category of techniques covers the static mechanical tests (loading in uniaxial, triaxial compression/tension, oedometric test etc.) on specimens that have hardened inside a mold in test rigs for aging, in pressure and temperature, and are then unloaded in order to be put in a measuring instrument. These tests require the specimens to be brought back to atmospheric pressure and room temperature, in order to equip them with measurement sensors, position them under a press, and then perform the tests proper, after optionally returning the specimens to conditions of temperature and pressure similar to those encountered in the well. These cycles of loading/unloading may not only damage the specimens prior to measurement, but also disturb measurement of the characteristics of said specimens. Moreover, this first category of techniques does not allow testing of very young cements, as it is necessary to wait for the cement specimen to be removed from its mold in order to be tested. Finally, owing to their destructive nature, these techniques only allow measurement at a point in time, and do not offer the possibility of ascertaining the evolution of the mechanical parameters over time, as a function of hydration of the cement.

A second category of techniques covers the dynamic tests based on measurement of the propagation of ultrasonic waves, and not comprising return of the specimens to ambient conditions. These techniques are, however, of limited interest owing to their indirect character. In particular, the static parameters, which are the parameters used for simulating the behavior of the cement sheaths or plugs over their life, are only accessible indirectly: they are calculated from the dynamic parameters, determined on the basis of measurement of the ultrasonic waves, using correlation formulas; these formulas themselves are obtained from static tests, which may be faulty, or may not cover the field of application of the materials being tested. In fact, these static tests are generally performed on cubic specimens of cement in certain conditions of pressure and temperature that do not necessarily correspond to the conditions of the dynamic tests. These techniques include measurements of the Ultrasonic Cement Analyzer UCA type. Measurements of the UCA type consist of measuring the velocity of the compression waves and using a correlation to evaluate the compressive strength of the cement.

A third category of techniques comprises some proposals for static mechanical tests without a loading/unloading step as mentioned above that requires return of the cement specimen to ambient pressure and temperature before taking the measurements.

Thus, document EP 1541987 describes a system in which a cement composition is cast in a bone-shaped mold, where the specimen is aged under temperature and under pressure, and is loaded in uniaxial tension until the specimen breaks, without having to unload the specimen. However, this method does not allow measurements to be taken in in-situ conditions, as the pressure can only be exerted on two faces of the specimen, the other faces being subjected to a condition of loading by reaction of the mold and not by application of stresses in in-situ conditions. The measurements are therefore biased. Moreover, only tensile tests are possible, the latter being biased with respect to measurement of the elastic constants relative to the compressive tests, owing to the appearance of microcracks that invalidate the assumption of elasticity. The range of determination of the elastic parameters is therefore greatly reduced. Moreover, it is not possible to measure the parameters of rupture in compression, nor measure the parameters at young age of the cement. Finally, the geometry used is not conventional.

Document U.S. Pat. No. 7,621,186 describes a variant of the preceding system, adopting a geometry of the truncated type. It therefore suffers from the same drawbacks.

Document WO 2007/020435 proposes a technique that consists of causing the cement composition to set in an annular space located between two concentric tubes, then varying the pressures at intrados of the inner tube and/or at extrados of the outer tube while measuring the strains induced. This technique cannot be used for tests in axial compression. Moreover, this technique has the drawback of being based on measurement in a heterogeneous stress field (in elasticity, the fields of stresses and strains in a hollow cylinder vary as $1/r^2$). Thus, measurement of the elastic properties of the specimen is very imprecise (very error-prone), just like measurement of the properties of specimen damage and rupture.

Document U.S. Pat. No. 7,089,816 describes a technique that consists of causing the cement composition to set in a cylindrical envelope, consisting of a deformable membrane and two pistons, placed in a confining enclosure. Then the mechanical tests are begun directly, by applying a confining pressure via the membrane and axial loading by the pistons, as for a conventional triaxial cell. A drawback of this technique is that the use of a flexible membrane for setting of the cement leads to a specimen of irregular shape after setting. Owing to the volume changes associated with setting, in fact Taylor instabilities develop, causing the specimen to lose its initial geometry. Moreover, with this technique it is not possible to perform measurements in accordance with the existing procedures, as hydration of the cement is not reproduced correctly.

Document U.S. Pat. No. 7,549,320 corresponds to a technique of the same type, with a variation of the loading technology. Setting of the specimen takes place, as in U.S. Pat. No. 7,089,816, inside a flexible membrane. The rigid confining enclosure surrounding the flexible membrane is compartmented owing to active sealing devices, and allows application of a differential pressure to the specimen, by injecting fluids. The flexible membrane used in this device may, moreover, be semipermeable, thus limiting specimen deformation while it sets, but disturbing the process of hydration of the cement specimen.

Document U.S. Pat. No. 7,552,648 describes yet another variant, in which a fluid is injected into the specimen itself, which is porous, in order to obtain the desired pressure. Then a tensile test is carried out. No compressive test is envisaged, and the external supply of fluid does not correctly simulate the water exchanges in in-situ conditions, as is also the case for the technique according to document U.S. Pat. No. 7,549,320.

Besides the drawbacks mentioned above for this third category of techniques, with tests of this type it is not possible to perform measurements on very young cements, i.e. starting from the first hours of hydration, nor monitor the evolution of the mechanical parameters measured over time, as a function of hydration of the cement.

None of the three categories of techniques described allows artifact-free measurement of the mechanical properties of a cement during setting.

AIMS OF THE INVENTION

There is consequently a need for a method for determining the mechanical parameters of a cement system and their evolution over time, in in-situ conditions, that does not have the drawbacks of the measurement techniques described above.

The invention aims to meet a need for simple characterization of the mechanical behavior of a cement system, by determining static mechanical properties and hydro-mechanical properties expressed as a function of time, and as a function of different pressures and temperatures corresponding to the conditions encountered along a wellbore.

Another aim of the invention consists of supplying a method that can easily be applied industrially for characterizing the mechanical behavior of a cement system, which uses simple measurements that can be standardized.

Another aim of the invention consists of supplying a method for estimating the evolution of the mechanical parameters of a cement system over time, from the start to the end of hydration thereof.

The invention also aims to provide estimation of the static mechanical parameters of the cement, which constitute the parameters used for reliable simulation of the mechanical behavior of cement sheaths or plugs over their life.

BRIEF DESCRIPTION OF THE DRAWINGS

In FIG. 6, α(t) is shown for a low pressure of 0.3 MPa and at different temperatures (7° C., 13° C., 25° C., 40° C. and 60° C.). In FIG. 7, α(t) is shown at higher pressures, for the following pressure/temperature pairs: (40 MPa, 30° C.), (40 MPa, 15° C.), (20 MPa, 30° C.). In FIG. 8, α(t) is shown for the following two pressure/temperature pairs: (0.3 MPa, 60° C.), (20 MPa, 60° C.).

DETAILED DESCRIPTION OF THE INVENTION

Figure 1:
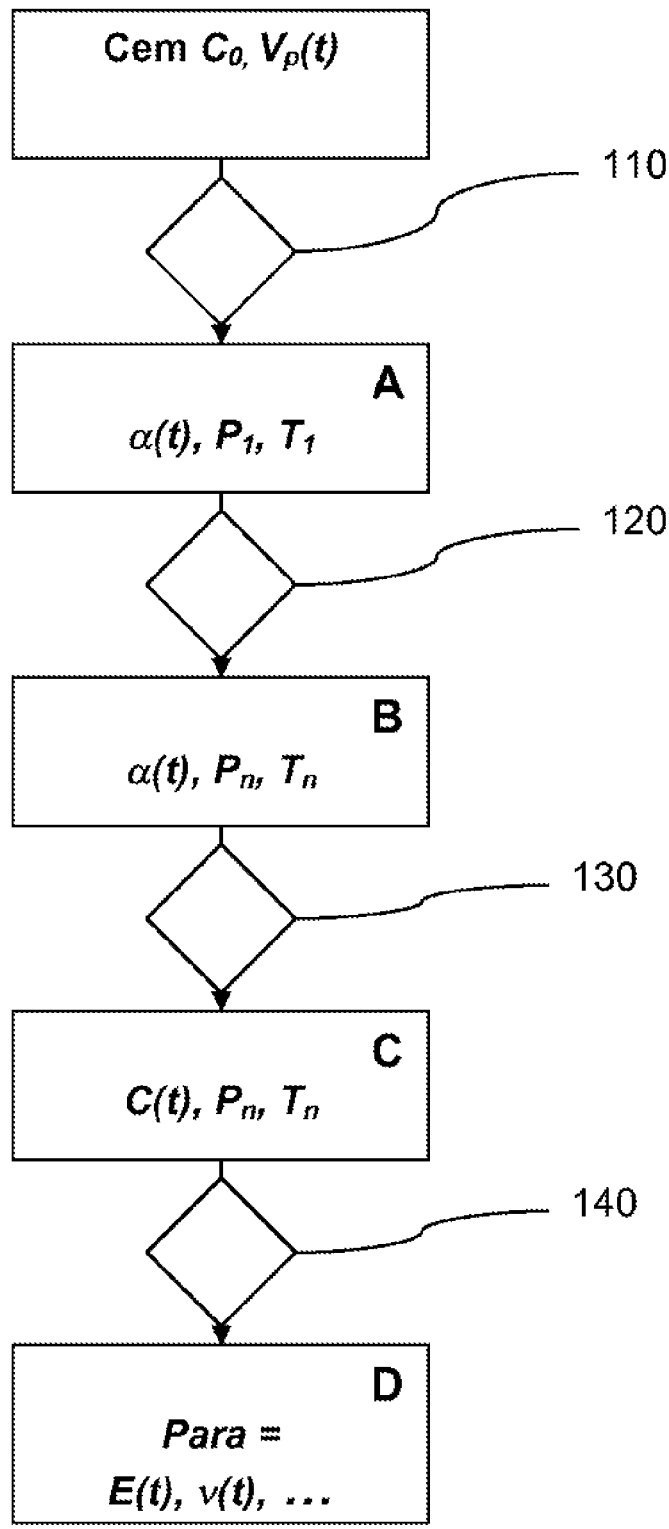
FIG. 1 shows the logic diagram of the method according to the invention.

In the description of the invention and the particular examples of the invention that follow, reference is made to the appended drawings.

To achieve at least one of the aforementioned aims, among others, the present invention proposes a method for determining mechanical parameters of a cement system of initial composition $C_0$ and of fineness Φ, as a function of time, and as a function of the fineness of the cement system, the pressure and/or the temperature. This method comprises the following steps:

(A) determining the degree of hydration of the cement system as a function of time α(t) from the velocity of the compression waves as a function of time $V_p(t)$ measured in a specimen of the cement system, at a pressure $P_1$ and a temperature $T_1$;

(B) determining the degree of hydration α(t) as a function of desired values of fineness $Φ_n$ of the cement system, of pressure $P_n$ and/or of temperature $T_n$;

(C) determining the composition of the cement system as a function of time C(t) and as a function of desired values of fineness $Φ_n$ of the cement system, of pressure $P_n$ and/or of temperature $T_n$, from the degree of hydration α(t) determined in step B;

(D) determining at least one mechanical parameter of the cement system as a function of time, and as a function of desired values of fineness $Φ_n$ of the cement system, of pressure $P_n$ and/or of temperature $T_n$, from the composition of the cement system C(t) determined in step C.

According to one embodiment of the invention, the method makes it possible to characterize the mechanical behavior of a cement system used as cement sheath or plug in a well, preferably an oil well. The method according to the invention is not limited to this use, and may be employed in the context of any design of well comprising a cement sheath or a cement plug for which characterization of the mechanical behavior of the cement system used is desired, for example in the area of gas storage or geothermal energy.

Definitions

Throughout the present account, unless expressly stated otherwise, a singular must be interpreted as a plural and vice versa.

The following definitions are given as examples, to facilitate interpretation of the present account.

A cement system in the sense of the present invention corresponds to a cement slurry or a hardened cement.

Cement slurry means a fluid composition (liquid, pasty, granular, etc.) based on cement and water, which can harden, i.e. can be transformed to a solid or almost solid state in course of time (by undergoing a hardening step). The expression "cement grout" is used as a synonym of cement slurry. Thus, hardening corresponds in this case essentially to hydration (or setting) of the composition based on cement and water.

Hardened cement means a cement slurry that has undergone hardening, and in which a porous skeleton has begun to develop, able to endow it with mechanical strength. In the sense of the invention, a hardened cement is not necessarily a fully hardened cement, i.e. in which hydration is completed. A fully hardened cement is a cement whose hydration is 100% complete.

Static mechanical parameter means a parameter that is not obtained from measurement of velocities of waves. The static parameters constitute the parameters used for reliable simulation of the mechanical behavior of the cement sheaths or plugs over their life, contrary to the dynamic parameters. The latter, generally obtained from methods of measurement of sonic/ultrasonic waves, diverge from the static parameters, owing to the dependence on the mechanical properties of the cement at the frequency of the waves used and on the size of the cement specimens tested.

Fineness of a cement means the fineness of grinding of a cement expressed by its specific surface (developed surface per unit mass, expressed in $cm^2/g$), and measured using apparatus of the Blaine type according to standard NF EN 196-6.

Compression waves or P waves means sonic or ultrasonic waves created by the mechanical vibration of a fluid or solid support and propagated owing to the elasticity of the surrounding medium in the form of longitudinal waves.

The term initial, used for example in reference to the composition of the cement system, to the temperature, pressure or any other physicochemical parameter considered in the present description, refers to the initial stage of the cement system in the form of a cement slurry, and in which the hydration reactions have not or have barely started, corresponding to the initial time t=0.

Reactive initial phase means an initial phase of the cement of the cement system, able to undergo hydration to give a hydrated phase, also called hydrate in the present description.

The Cement System

The method according to the present invention applies to all cements for which hydration takes place through a series of exothermic chemical reactions between its components and water, for example Portland cements, high-alumina cements, and other cements defined according to standards EN-196-2, EN-196-6, EN196-7, ISO 3310-1, ISO 13500, and the standards ISO 10426-1 to ISO 10426-6 as regards the petroleum industry.

The cement system according to the present invention may comprise admixtures, enabling the desired properties to be obtained:

accelerators (example: calcium chloride), which have the aims of reducing the induction period of the cement system, and optionally of accelerating the development of uniaxial compressive strength;

retarders (example: lignosulfonates), which have the aim of increasing the induction period of the cement system;

extenders (example: bentonite, hollow beads), which have the aim of lowering the density of the cement slurry and/or reducing the concentration of cement or increasing the concentration of water;

weighting agents (example: hematite) which have the aim of increasing the density of the cement slurry;

dispersants (example: lignosulfonates), which have the aim of lowering the viscosity of the cement slurry by deflocculating the cement grains;

filtration loss controllers (example: latex), which have the aim of limiting the transfers of water from the cement slurry to the external system by constructing a cake with little or no permeability against the formation;

loss controllers (example: gilsonite), which have the aim of limiting the losses of cement in very permeable zones;

salt;

special admixtures, such as antifoaming agents, fibers, expanding agents, antigas agents, antisedimentation agents, or agents giving resilient cements.

The cement system according to the present invention comprises an initial composition $C_0$ at time point t=0. This initial composition $C_0$ comprises the initial phases of the cement, including at least one reactive initial phase that may undergo hydration, and the initial water, according to given fractions, for examples that are expressed by volume. At time point t, hydration of the cement system is advanced, and the cement composition C(t) is different from the initial composition $C_0$. The cement composition C(t) comprises m phases, including the initial phases of the cement in proportions different from $C_0$, at least one hydrated phase resulting from the hydration of at least one reactive initial phase of the cement, and water.

According to one embodiment of the invention, the cement of the cement system comprises at least one reactive initial phase X, preferably selected from the group consisting of tricalcium silicate of formula $3CaO.SiO_2$ (alite), with the symbol $C_3S$, dicalcium silicate of formula $2CaO.SiO_2$ (belite), with the symbol $C_2S$, tricalcium aluminate of formula $3CaO.Al_2O_3$ (aluminate), with the symbol $C_3A$, tetracalcium aluminoferrite $C_4F$, and combinations thereof. According to this embodiment, the cement of the cement system comprises at least one hydrated phase resulting from the hydration of at least one reactive initial phase of the cement, preferably selected from the group consisting of hydrated calcium silicate C—S—H, calcium hydroxide CH, hydrated calcium trisulfoaluminate TSA (ettringite), hydrated calcium monosulfate AFm, hydrated calcium aluminoferrite, and combinations thereof.

The initial phases such as the silicates $C_3S$, $C_2S$ and the aluminates are reactive phases that react with the water of the cement system to give hydrated phases, by exothermic chemical reactions. The silicates react with water to form hydrated calcium silicates C—S—H, and calcium hydroxide CH (portlandite of formula $Ca(OH)_2$). The aluminates react with water and with gypsum, or with water alone to form the following hydrated aluminates: hydrated calcium trisulfoaluminate TSA (ettringite), hydrated calcium monosulfate AFm and hydrated calcium aluminoferrite.

The microstructure of the cement system, especially of hardened cement, is very complex. The volume fractions, possibility of crystallization, morphology and dimensions of the hydrated phases of hardened cement are presented in Table 1 below, relating to a Portland cement (Bernard et al.[12]).

TABLE 1

| Mineralogical phase | Volume fraction (%) | Possibility of crystallization | Morphologies | Dimensions |
|---|---|---|---|---|
| C-S-H | 50-70 | Very slight | Not resolved | 10-100 μm |
| CH | 15-20 | Very good | Hexagonal solid | 10-100 μm |
| Ettringite | 1-5 | Good | Solid of acicular form | 10 × 0.5 μm |
| Monosulfoaluminate | 1-5 | good | Solid in the form of hexagonal plates | 1 × 1 × 0.1 μm |

Portlandite CH is formed of broad hexagonal crystals that are surrounded by the C—S—H phase, which is in the form of gel, and occupies about 20% of the volume of the hardened cement. The monosulfoaluminates and ettringite play a minor role in the structure of hardened cement and generally represent a volume fraction from 15% to 20%. The C—S—H phase constitutes the major product of hardened cement. The C—S—H phase is a porous phase, of amorphous, colloidal structure, and has a varied chemical composition. It occupies between 50% and 70% of the total volume of hardened cement, giving the properties of this phase a dominant role in the macroscopic properties of the cement system. The C—S—H phase exists in two forms: the "high-density" phase C—S—H HD (also called "HD" in the present description) and the "low-density" phase C—S—H LD (also called "LD" in the present description). Each of these two forms has, according to Jennings et al.[8,9], a common unit called a globule. The difference between these two types of C—S—H consists of the arrangement of the globules, resulting in different porosities depending on the type of C—S—H: about 24% for C—S—H HD, with a pore size between about 10 nm and 100 nm))(Constantinides[10]), and about 37% for C—S—H LD, with a pore size between about 5 nm and 50 nm.

According to one embodiment of the invention, the cement system comprises Portland cement, which is one of the commonest cements, comprising the following initial phases used (see standards EN-196-2, EN-196-6, EN196-7, ISO 3310-1, ISO 13500, and the standards ISO 10426-1 to ISO 10426-6 for the contents of initial phases, depending on the class and grade of cement):

tricalcium silicate of formula $3CaO.SiO_2$ (alite), with the symbol $C_3S$;

dicalcium silicate of formula $2CaO.SiO_2$ (belite), with the symbol $C_2S$;

tricalcium aluminate of formula $3CaO.Al_2O_3$ (aluminate), with the symbol $C_3A$;

tetracalcium ferroaluminate of formula $4CaO.Al_2O_3$ $Fe_2O_3$ (ferrite), with the symbol $C_4F$;

calcium sulfate dihydrate $CaSO_4.2H_2O$ (gypsum).

The silicate phases and the aluminates are obtained from a ground clinker, the main constituent of Portland cement.

Of course, the method according to the invention is not limited to the cement system comprising a Portland cement. In particular, the method may be adapted for determining mechanical parameters of various cement systems, with chemical compositions and hydration reactions different from those of a cement system comprising a Portland cement, while remaining within the scope of the invention.

The Hydration Process of the Cement System

The method according to the invention takes into account different stages of the process of hydration of a cement system for determining at least one mechanical parameter of the latter. The hydration process may be monitored from the variation of the thermal flux created by the exothermic reactions of hydration of the reactive initial phases of the cement with water.

The quantity of heat released by the exothermic reactions during hydration of the cement system can be measured using a calorimeter. Two types of calorimeter are generally used. The first type corresponds to the quasi-adiabatic calorimeters, in which the reaction takes place inside a chamber that is perfectly insulated thermally. This type of calorimeter is not suitable for measuring specimens of cement systems under high pressures, and the maximum pressure for use is about 0.1 MPa. A second type corresponds to the isothermal calorimeters, with which the tests are carried out in a space of the order of a cubic centimeter, and where the temperature is controlled so that the temperature of the space does not vary. The materials used for this type of measuring instrument allow working with higher pressures, of the order of a megapascal.

In general, several stages can be identified in the process of hydration of a cement system. Classically, hydration of the cement system comprises, in this order:

a period of dissolution, during which there is dissolution of the ettringite and formation of CSH gel;

a dormant period, also called induction period, during which there is an increase in the concentration of $C_3A$ and of $OH^-$ ions;

a period of rapid formation of C—S—H and of portlandite CH, also called the period of acceleration;

a period of slowing of the formation of C—S—H and of portlandite CH; and of possible formation of monosulfoaluminate;

and a period of curing, also called period of diffusion, where the chemical reactions are controlled by diffusion phenomena.

Figure 2:
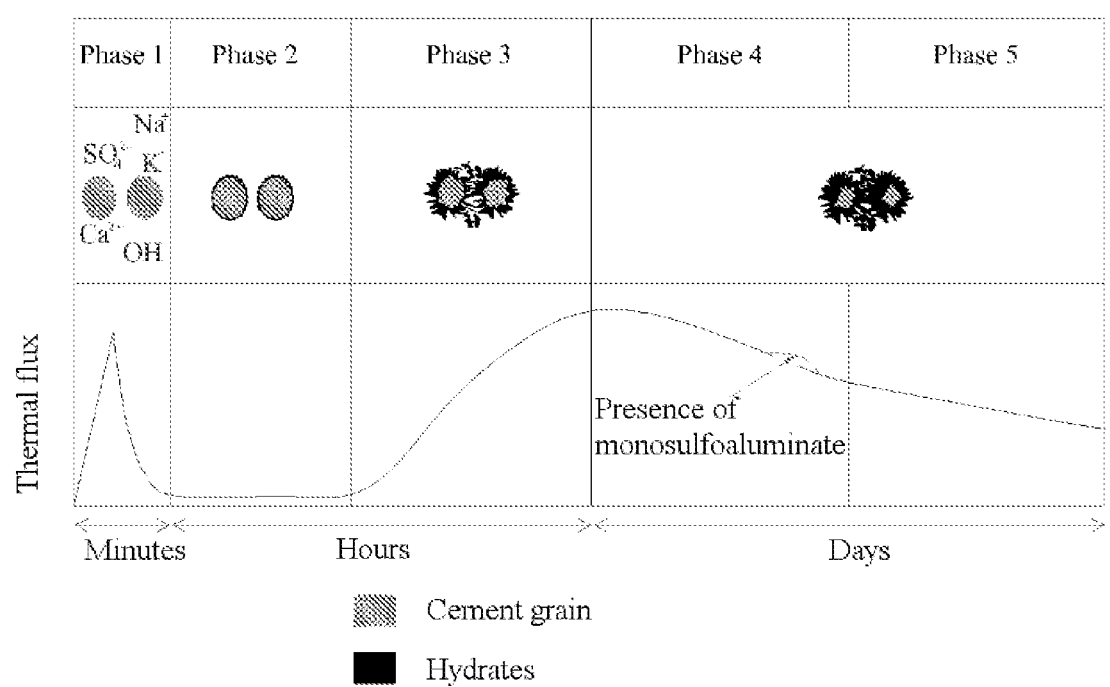
FIG. 2 is a schematic diagram illustrating the different stages of the process of hydration of a Portland cement.

FIG. 2 illustrates the hydration process in the case of a Portland cement (Rixom et al.[15]). In this case, the hydration process is generally divided into 5 steps. Each step corresponds to a tendency for evolution of heat caused by the hydration reactions:

Period 1: a period of initial hydration continues for about 15 minutes, during which the most soluble chemical constituents ($Na_2SO_4$, $K_2SO_4$, $CaSO_4.xH_2O$) of the cement dissolve, causing the pH of the cement slurry to increase.

Period 2: a dormant period then follows, for about 4 hours. The heat of hydration barely changes. The strength of the cement paste has not yet developed.

Period 3: this third period corresponds to an acceleration of hydration, which lasts about 4 hours. During this period, there is very rapid evolution of the heat of hydration. The hydrates formed come into contact with one another, which forms the strength of the paste.

Period 4: a period of slowing then sets in and lasts for some days. The evolution of the heat of hydration becomes slower.

Period 5: a period of curing is observed for several months after the start of setting of the cement system, and the variation of the amount of hydrates gradually stabilizes.

The evolution of hydration of the cement system over time is conventionally described by the evolution of the degree of hydration over time $\alpha(t)$, which is an intrinsic parameter, the value of which varies from 0 to 1. At time point t, it can be evaluated as the ratio of the quantity of heat $Q(t)$ produced by the chemical reactions at time point t to the total quantity of heat $Q(t=\infty)$ produced when the chemical reactions have all taken place. The hydration kinetics varies over the course of the hydration process. Among the periods of the hydration process, a first stage in which hydration is mainly governed by a process of nucleation and growth, such as described for example by Avrami[3], is recognized conventionally. A second stage of the process of hydration of the cement system is characterized by hydration governed mainly by an ion diffusion process. This second stage begins when the degree of hydration $\alpha$ reaches a value of a threshold degree of hydration $\alpha^*$. During the first stage, governed by the phenomena of nucleation and growth, a layer of hydrates is created around the cement grains, and is relatively permeable, which allows diffusion of ions and progress of the chemical reactions. When a threshold degree of hydration $\alpha^*$ is reached, there is a decrease in ion diffusion, connected with thickening of the layer of hydrates around the cement grain and decrease in permeability of this layer. It is then ion diffusion that controls the progress of the reactions (Kondo and Kodama[4]; Fuji and Kondo[5]). In the case of the process of hydration of a Portland cement, as shown in FIG. 2, the threshold degree of hydration $\alpha^*$ marks the transition from period 4 to period 5. Periods 3 and 4 correspond to the stages of nucleation and growth according to Avrami[3], and period 5 (period of curing) is mainly governed by the ion diffusion process.

Tricalcium silicate $C_3S$ and dicalcium silicate $C_2S$ react with water according to the following equations, from Jennings et al.[6]:

$$2C_3S + 10{,}6H \rightarrow C_{3,4}\text{—}S\text{—}H_8 + 2{,}6CH$$

$$2C_2S + 8{,}6H \rightarrow C_{3,4}\text{—}S_2\text{—}H_8 + 0{,}6CH \quad (I)$$

The hydrated phases C—S—H and CH form the principal constituents of hardened cement, and are mainly responsible for the solidity of hardened cement. The hydration kinetics of the $C_3S$ phase is quicker than that of the $C_2S$ phase, and the amount of CH created by hydration of $C_3S$ is about three times greater than that created by the hydration of $C_2S$. Thus, the $C_3S$ phase plays a major role in the hydration process and in the development of the mechanical behavior of the cement system, by initiating the strength of the cement paste during the first few days.

According to one embodiment of the invention, the method takes into account the two reactions (I) described above for simulating the hydration process.

Nature of the Mechanical Parameters Determined by the Method According to the Invention The invention aims to characterize the mechanical behavior of a cement system, and notably to determine certain mechanical parameters and their evolution over time, in in-situ conditions, which it will then be possible to use, for example, for modeling the behavior of the cement sheaths or plugs of the wellbore over their life. The method according to the invention makes it possible to determine at least one mechanical parameter of the cement system as a function of time, for desired values of fineness $\Phi_n$ of the cement system, of pressure $P_n$ and/or of temperature $T_n$.

According to one embodiment of the invention, the method makes it possible to determine at least one mechanical parameter, which is selected from the static deformability parameters, preferably the static elastic parameters such as static Young's modulus E, static Poisson's ratio ν, bulk modulus K, shear modulus G, and combinations thereof, for example the oedometric modulus $K_v$, or Lamé's modulus λ. Preferably, two static elastic parameters are determined. Advantageously, it is possible to describe the elastic properties of the cement system, determined solely from the combination of two static elastic parameters, using formulas that are well known in elasticity, as described in Table 2 below.

such parameters of hydro-mechanical coupling notably makes it possible to determine the static deformability parameters, preferably the static elastic parameters, in nondrained conditions, on the basis of knowledge of the static elastic parameters, in drained conditions. These parameters may, for example, be used for simulating the behavior of a cement sheath whose pores are saturated with water when the rate of loading is much faster than the rate of diffusion of the pore pressures. The set of formulas (II) used for going from the drained static elastic properties (subscript d) to the nondrained static properties (subscript u), and vice versa, is given below.

$$v_d = \frac{3v_u - (1 + v_u) \cdot bB}{3 - 2(1 + v_u) \cdot bB} \quad \text{(II)}$$

TABLE 2

| K | E | λ | ν | $K_v$ | G |
|---|---|---|---|---|---|
| $\lambda + \frac{2G}{3}$ | $G\frac{3\lambda + 2G}{\lambda + G}$ | — | $\frac{\lambda}{2(\lambda + G)}$ | $\lambda + 2G$ | — |
| — | $9K\frac{K - \lambda}{3K - \lambda}$ | — | $\frac{\lambda}{3K - \lambda}$ | $3K - 2\lambda$ | $\frac{3}{2}(K - \lambda)$ |
| — | $\frac{9KG}{3K + G}$ | $K - \frac{2G}{3}$ | $\frac{3K - 2G}{2(3K + G)}$ | $K + \frac{4G}{3}$ | — |
| $\frac{EG}{3(3G - E)}$ | — | $G\frac{E - 2G}{3G - E}$ | $\frac{E}{2G} - 1$ | $G\frac{4G - E}{3G - E}$ | — |
| — | — | $3K\frac{3K - E}{9K - E}$ | $\frac{3K - E}{6K}$ | $3K\frac{3K + E}{9K - E}$ | $\frac{3KE}{9K - E}$ |
| $\lambda\frac{1 + \nu}{3\nu}$ | $\lambda\frac{(1 + \nu)(1 - 2\nu)}{\nu}$ | — | — | $\lambda\frac{1 - \nu}{\nu}$ | $\lambda\frac{1 - 2\nu}{2\nu}$ |
| $2G\frac{1 + \nu}{3(1 - 2\nu)}$ | $2G(1 + \nu)$ | $2G\frac{\nu}{1 - 2\nu}$ | — | $2G\frac{1 - \nu}{1 - 2\nu}$ | — |
| — | $3K(1 - 2\nu)$ | $3K\frac{\nu}{1 + \nu}$ | — | $3K\frac{1 - \nu}{1 + \nu}$ | $3K\frac{1 - 2\nu}{2(1 + \nu)}$ |
| $\frac{E}{3(1 - 2\nu)}$ | — | $\frac{E\nu}{(1 + \nu)(1 - 2\nu)}$ | — | $\frac{E(1 - \nu)}{(1 + \nu)(1 - 2\nu)}$ | $\frac{E}{2(1 + \nu)}$ |

According to one embodiment of the invention, at least one mechanical parameter determined according to step D, in particular selected from the static deformability parameters, preferably the static elastic parameters, is a parameter in drained conditions. In a drained system, it is assumed there is circulation of the pore fluids, for example liquids, between the cement system and its environment (enveloping) to keep the pore pressure constant. Otherwise, in a system that is not drained, it is assumed there is no exchange of pore fluids between the cement system and its environment. The value of the mechanical parameters of the cement system, especially of the parameters of static deformability, will be different depending on whether the system is or is not drained.

According to another embodiment, the method further comprises determination of at least one parameter of hydromechanical coupling, such as Biot's coefficient b or Skempton's coefficient B, and combinations thereof. Knowledge of -continued $$v_u = \frac{3v_d - (1 + 2v_d) \cdot bB}{3 - 2(1 - 2v_d) \cdot bB}$$

$$E_d = \frac{3(1 - bB)}{3 - 2(1 + v_u) \cdot bB} \cdot E_u$$

$$E_u = \frac{3E_d}{3 - (1 - 2v_d) \cdot bB}$$

$$K_d = (1 - bB) \cdot K_u$$

$$K_u = \frac{K_d}{1 - bB}$$

Young's modulus E and Poisson's ratio ν are elastic constants that are determined classically in a test of uniaxial or triaxial compression where a cylindrical specimen of slenderness ratio 2 is submitted to an increase in axial stress but no confinement is applied and the pore pressure is constant. These coefficients are then defined classically, in the zone where the strains are reversible, by the following formulas: $E=\Delta\sigma_{axial}/\Delta\epsilon_{axial}$, $\nu=-\Delta\epsilon_{radial}/\Delta\epsilon_{axial}$, where $\Delta\sigma_{axial}$ is the increment of axial stress, $\Delta\epsilon_{axial}$ the increment of axial strain and $\Delta\epsilon_{radial}$ is the increment of radial strain.

The bulk modulus K is an elastic constant determined classically in a test of isotropic compression where a specimen is submitted to an increase in axial stress equal to the increase in confinement (called isotropic stress) while the pore pressure is constant. This coefficient is then defined classically, in the zone where the strains are reversible, by the following formula: $K=\Delta\sigma_{isotropic}/\Delta\epsilon_{volume}$, where $\Delta\sigma_{isotropic}$ is the increment of isotropic stress and $\Delta\epsilon_{volume}$ is the increment of volume strain.

The shear modulus G is not generally measured directly, although it may be theoretically, and is evaluated from knowledge of two other elastic parameters.

The oedometric modulus $K_v$ is an elastic constant determined classically in a test of oedometric compression where a cylindrical specimen is submitted to an increase in axial stress while no radial displacement is allowed and the pore pressure is constant. This coefficient is then defined classically, in the zone where the strains are reversible, by the following formula: $K_v=\Delta\sigma_{axial}/\Delta\epsilon_{axial}$, where $\Delta\sigma_{axial}$ is the increment of axial stress and $\Delta\epsilon_{axial}$ is the increment of axial strain.

The method according to the invention makes it possible to determine the static deformability parameters, which have the advantage of being those used in the modeling of cement sheaths or plugs of wellbores. These static parameters must not be confused with the so-called "dynamic" parameters, which are evaluated from knowledge of the velocity of the compression waves and the shear rate.

The parameters of hydro-mechanical coupling are for example Biot's coefficient (b) and Skempton's coefficient (B). Biot's coefficient (b) is the coefficient used for defining the effective stress, i.e. the stress that induces the deformation of a material in the case when the pore pressure is not zero, and is expressed in the following relation: $\Delta\sigma'=\Delta\sigma-b\cdot P_p$, where σ' is the effective stress, σ is the total stress, and $P_p$ is the pore pressure. Skempton's coefficient (B) is the coefficient used for calculating the pressure change due to a change in isotropic stress without expulsion of fluid for a saturated specimen, and is expressed according to the relation $\Delta P_p=B\cdot\Delta\sigma$, in which $\Delta\sigma$ is the change in isotropic stress, and $\Delta P_p$ is the change in pore pressure.

According to the method of the invention, these parameters can be determined for the cement system starting from its youngest age, which notably allows better modeling of the mechanical behavior of the cement system. It may be important to know the behavior of the cement in the early stage in the context of drilling operations, for example for operations which it must be possible to carry out quickly after pumping the cement slurry into the well, such as thermal logs for locating the top of the column of cement, additional drilling operations once the casing is in place, perforation of the production zones, or for evaluating the stress state in the cement sheath once the cement has hardened.

The Method

The flowchart in FIG. 1 shows the method according to the invention schematically, comprising steps A to D described below.

The cement system tested by the method according to the invention has a known initial composition $C_0$ and a fineness Φ. Another initial parameter used by the method according to the invention is the velocity of the compression waves in the cement system as a function of time $V_p(t)$. Knowledge of these initial parameters makes it possible, thanks to the method according to the invention, to determine at least one mechanical parameter of the cement system.

The method according to the invention is not limited to the combination of steps A to D, in the order stated, and intermediate steps may be carried out, while remaining within the scope of the invention.

Step of Measurement of the Velocity of the Compression Waves of the Cement System as a Function of Time According to one embodiment of the invention, the method further comprises an initial step of measurement of the velocity of the compression waves as a function of time $V_p(t)$ in a specimen of the cement system. Such a measurement may, for example, be carried out by a method of the Ultrasonic Cement Analyzer UCA type, as described for example in U.S. Pat. No. 4,259,868. The methods of the UCA type are well-known methods for evaluating the quality of a cement system, and form part of the second category of methods of measurement described above, for characterizing the mechanical behavior of a cement system. They are nondestructive methods allowing analysis of cement specimens, in the form of cement grout, using measurement of the velocity of ultrasonic waves, notably of compression, passing through the specimen, without the need to bring the specimens to the environmental conditions (pressure and temperature) of the laboratory prior to measurement. An improvement of the methods of the UCA type makes it possible, moreover, to measure the velocities of the shearing waves, and are designated as MPRO measurements (Reddy et al.[7]). The velocity of the compression and shearing waves as a function of time thus recorded allows calculation on the one hand of the uniaxial compressive strength, linked to the velocity of the compression waves by a correlation function, and on the other hand the dynamic elastic parameters, from the following relations:

Dynamic Poisson's ratio:

$$\nu_{dyn} = \frac{\frac{1}{2} - \left(\frac{V_S}{V_P}\right)^2}{1 - \left(\frac{V_S}{V_P}\right)^2} \tag{III}$$

Dynamic Young's modulus:

$$E_{dyn} = \text{density} \times \frac{V_P(1+\nu_{dyn})\cdot(1-2\cdot\nu_{dyn})}{(1-\nu_{dyn})} \tag{IV}$$

Figure 3:
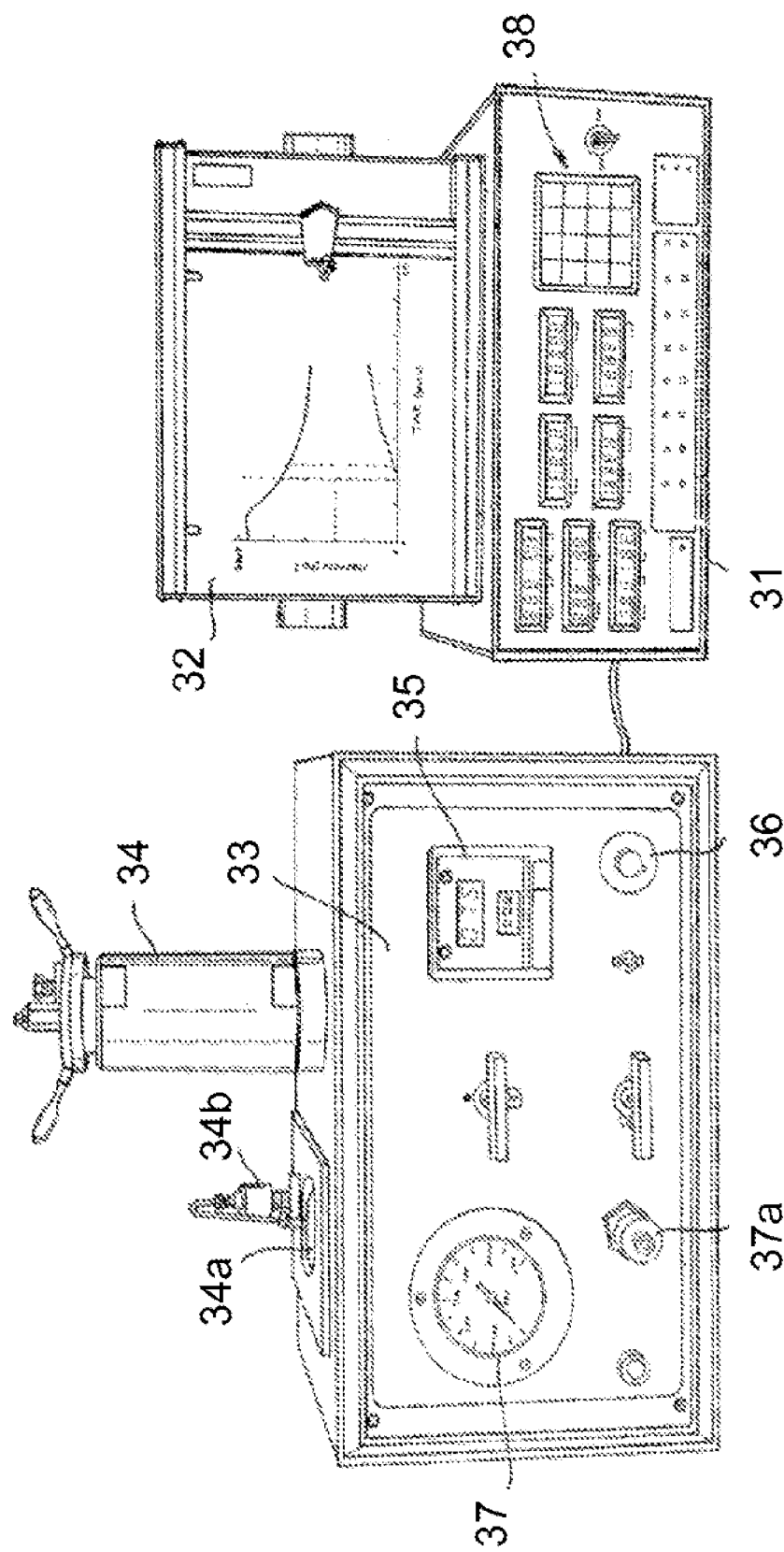
FIG. 3 presents an example of a device of the Ultrasonic Cement Analyzer type (UCA) for measuring the velocity of the compression waves in a cement specimen used in the method according to the invention.

FIG. 3 shows a measuring instrument of the UCA type, as described in U.S. Pat. No. 4,259,868. A measuring device of this kind comprises a measuring cell 34 intended to receive the cement grout and to be put under pressure. This cell 34 is put under pressure in an autoclave 33 by inserting it in an opening 34a and connection to a pressurizing line 34b. The autoclave pressure and temperature, transmitted to cell 34, are controlled by variators (37a, 36) and monitors (37, 35). Ultrasonic transducers (not shown) are coupled to the measuring cell 34, for emitting and receiving ultrasonic waves that pass through the specimen of the cement system. A control computer 31 is connected to the autoclave and comprises a keyboard 38 for input of data and control functions into the measuring device, and a digital plotter 32 for visualizing the velocity of the measured waves as well as the uniaxial compressive strength calculated in real time.

The measurement protocol according to a method of the UCA or MPRO type follows the following scheme:
preparation of a volume of cement slurry;
filling of the measuring cell;
conditioning the specimen of the cement system by applying a ramp of increase in pressure and temperature to reach the in-situ conditions ($P_1$, $T_1$). Once these conditions have been reached, the pressure and the temperature remain constant;
measurement, as a function of time, of:
the velocity of the compression waves, and of velocity of the shearing waves in the case of a measurement of the MPRO type;
the pressure; and
the temperature; and use of a correlation function for evaluating the uniaxial compressive strength of the cement system as a function of time, and use of relations (III) and (IV) described above, for evaluating the dynamic Poisson's ratio and the dynamic Young's modulus as a function of time in the case of an MPRO measurement;
on completion of the test, removal of the test specimen and observation of the cement specimen.

It is to be understood that the invention is not limited to measurement of $V_p(t)$ by the methods of the UCA and MPRO type described here, and that a person skilled in the art will be able to select any method permitting measurement of the velocity of the compression waves of a cement system. Examples of such methods are described for example in the following documents: U.S. Pat. Nos. 5,859,811, 5,763,773, 5,357,481, 5,168,470, 5,001,676, 4,813,028, 4,779,236, 4,255,798, 3,401,773, and 2,538,114. It is also obvious that the method according to the invention can be carried out without having to perform this step of measurement of $V_p(t)$, if this data element is known anyway for the cement system under investigation.

One advantage of using measurement of the velocity of the compression waves is that this is a simple measurement that can be standardized, thus contributing to providing a method that can easily be applied industrially. The experimental protocol used for determining $V_p(t)$, if needed, is simple. It is only necessary to know the velocity of the compression waves to determine the mechanical behavior of a cement by the method according to the present invention.

Step A

Step A consists of determining the degree of hydration of the cement system as a function of time $\alpha(t)$, based on knowledge of the velocity of the compression waves $V_p(t)$ of the cement system in question, measured in a specimen of the cement system, at a pressure $P_1$ and a temperature $T_1$.

For this, the method according to the invention uses an empirical correlation 110 linking $\alpha(t)$ to $V_p(t)$.

According to one embodiment of the invention, the degree of hydration of the cement system as a function of time $\alpha(t)$ is calculated from $V_p(t)$ according to a linear relation. Preferably, the degree of hydration of the cement system as a function of time $\alpha(t)$ is calculated from $V_p(t)$ according to the following linear relation:

$$\alpha = \frac{(V_P - V_0)}{(V_\infty - V_0)} \quad (V)$$

with $V_0$ and $V_P$ corresponding respectively to the velocity of the compression waves measured in the specimen of the cement system at time t=0 and at time t, and $V_\infty$ corresponding to the velocity of the compression waves in the specimen of the fully hydrated cement system.

The values of $V_p$ and $V_0$ are known at the start of step A. The value of $V_\infty$ can be found experimentally by the same measurement as that for finding $V_p(t)$, and corresponds to a specimen in which hydration is complete. Knowing $V_p(t)$, $V_\infty$ is for example calculated using linear regression.

According to one embodiment of the invention, the value of $V_\infty$ is found from a model established on the basis of preliminary experimental data from tests of the UCA type, allowing this value to be predicted for any cement system. According to this embodiment, it is not necessary to undertake measurement of $V_\infty$ for the cement system considered by the method according to the invention.

According to one embodiment of the invention, $V_\infty$ is equal to about 3980 m/s.

Step B

The method according to the invention comprises a step B consisting of determining the degree of hydration $\alpha(t)$, resulting from step A, as a function of desired values of fineness $\Phi_n$ of the cement system, of pressure $P_n$ and/or of temperature $T_n$.

This determination uses a kinetic model 120 of the hydration of the cement system. According to a preferred embodiment of the invention, this kinetic model 120 comprises two stages corresponding to two substeps of step B: B-i and B-ii.

According to one embodiment of the invention, the hydration process comprises a first stage in which hydration is mainly governed by a process of nucleation and growth, and a second stage in which hydration is mainly governed by an ion diffusion process, said second stage starting when the degree of hydration $\alpha$ reaches a threshold value of the degree of hydration $\alpha^*$, this threshold value $\alpha^*$ being a function of the temperature. Step B comprises the following substeps:
(B-i) determination of the degree of hydration $\alpha(t)$ during the first stage of the process of hydration of the cement system;
(B-ii) determination of the degree of hydration $\alpha(t)$ during the second stage of the process of hydration of the cement system.

Each of the substeps B-i and B-ii takes into account the fineness $\Phi$ of the cement system, the pressure and the temperature for determining the degree of hydration $\alpha(t)$.

The method therefore advantageously takes into account the effects of temperature and pressure for simulating the evolution of the degree of hydration of the cement system.

According to one embodiment of the invention, the threshold value of degree of hydration $\alpha^*$ is evaluated by minimizing the difference between $\alpha(t)$, determined using the kinetic model 120, and $\alpha(t)$ determined experimentally from the velocity of the compression waves, for different temperatures, and at a constant pressure, so as to take into account the variation of $\alpha^*$ as a function of the temperature in step B. Advantageously, experimental determination of $\alpha(t)$ is carried out at different temperatures, and at a constant pressure less than or equal to 1 MPa, preferably less than or equal to 0.5 MPa, even more preferably less than or equal to 0.3 MPa. At such pressures, it can be considered that the effect of the activation volume is negligible.

Preferably:
the cement system of initial composition $C_0$ comprises a cement and water, the cement comprising at least one reactive initial phase X;

the degree of hydration α(t) determined in step B corresponds to the weighted average of the degrees of hydration of each of the reactive initial phases X of the cement;

the degree of hydration of each of the reactive initial phases X of the cement is a function of the ratio between the chemical affinity $A_X(\alpha)$ of the reactive initial phase X, said chemical affinity $A_X(\alpha)$ controlling the degree of evolution of hydration of the reactive initial phase X, and the characteristic time associated with the reaction of the reactive initial phase X with water $\tau_x$;

and the characteristic time associated with reaction of the reactive initial phase X with water $\tau_x$ is a function of the fineness Φ of the cement, the pressure and the temperature.

Advantageously, the characteristic time associated with reaction of the reactive initial phase X with water $\tau_x$ is expressed according to the following equation:

$$\tau_x(T, \Phi) = \sqrt[n_x+1]{\frac{\Phi_0}{\Phi}} \times \tau_x(T_0, \Phi_0) \exp\left(\frac{\Delta E_x}{R}\left(\frac{1}{T} - \frac{1}{T_0}\right) + \frac{\Delta V_x}{R}\left(\frac{P}{T} - \frac{P_0}{T_0}\right)\right) \quad \text{(VI)}$$

where $\Phi_0$ is the fineness of a reference cement, preferably $\Phi_0 = 3600$ cm²/g, $T_0$ is the initial temperature and $P_0$ is the initial pressure at time t=0 of the hydration process, R is the gas constant, $\Delta E_x$ is the activation energy, $\Delta V_x$ is the activation volume for nucleation and growth of the hydrates during the first stage of the hydration process, $n_x$ is a constant, determined experimentally, the values of which are published in the literature (Bernard et al.[12]).

Substep B-i

In substep B-i, the first stage of evolution of the degree of hydration is considered, where hydration is mainly governed by a process of nucleation and growth, as described for example by Avrami[3]. This first stage comprises the phases of acceleration and slowing of the hydration process in the case of a Portland cement. This substep B-i consists of determining the degree of hydration of the cement system from the degrees of hydration of each of the reactive initial phases X of the cement according to the following relation:

$$\alpha = \sum_{x=1}^{N} m^{x'} \cdot \alpha_x \quad \text{(VII)}$$

where N is the number of reactive initial phases X. For example, for the clinker, X would be one of the four main constituents of the clinker ($C_3S$, $C_2S$, $C_3A$, $C_4AF$). $M^{x_1}$ is the mass fraction of constituent X.

The degree of hydration of the reactive initial phase $\alpha_x$ is defined as the ratio of the amount of this phase that has reacted to the initial amount of this phase, and satisfies the following equation:

$$\frac{d\alpha_x}{dt} = \frac{A_x(\alpha)}{\tau_x} \quad \text{(VIII)}$$

The chemical affinity $A_x(\alpha)$ of the reactive initial phase X satisfies the following equation:

$$A_x(\alpha) = (1 - (\alpha - \alpha_{0x})) \cdot [-\ln(1 - (\alpha - \alpha_{0x}))]^{1 - \frac{1}{n_x+1}} \quad \text{(IX)}$$

where $n_x$ and $\alpha_{0x}$ are constants determined experimentally and known by a person skilled in the art (Bernard et al.[12]).

The characteristic time associated with reaction of the reactive initial phase X with water $\tau_x$ is a function of the fineness Φ of the cement, the pressure and the temperature. In the course of substep B-i, $\tau_x$ satisfies the following equation:

$$\tau_x(T, \Phi) = \sqrt[n_x+1]{\frac{\Phi_0}{\Phi}} \times \tau_x(T_0, \Phi_0) \exp\left(\frac{\Delta E_x}{R}\left(\frac{1}{T} - \frac{1}{T_0}\right) + \frac{\Delta V_x}{R}\left(\frac{P}{T} - \frac{P_0}{T_0}\right)\right) \quad \text{(VI)}$$

in which $\Phi_0$ is the fineness of a reference cement, preferably $\Phi_0 = 3600$ cm²/g, $T_0$ is the initial temperature and $P_0$ is the initial pressure at time t=0 of the hydration process, R is the gas constant, equal to 8.314 J° K−1 mol−1, $\Delta E_x$ is the activation energy, $\Delta V_x$ is the activation volume for nucleation and growth of the hydrates during the phases of growth and slowing of the hydration process, equal to −27×10⁻⁶ m³/mol, and $n_x$ is a constant determined experimentally and known by a person skilled in the art (Bernard et al.[12]).

The effects of the fineness of the cement system, of the pressure and of the temperature on the hydration kinetics of the latter are integrated in this equation (VI). This equation establishes that the rate of evolution of hydration of a cement system increases with the fineness, pressure and temperature.

Substep B-ii

In substep B-ii, the second stage of evolution of the degree of hydration is considered, where hydration is mainly governed by an ion diffusion process. This second stage comprises the curing phase in the case of a Portland cement.

We use r* to denote the value of the radius of the cement grain surrounded by a layer of hydrates when the degree of hydration of the cement reaches a threshold value α*. The value of the radius decreases with the progress of hydration, and its rate of decrease can be written as a function of a diffusion constant D (cm²/h) according to the following equation:

$$-\frac{dr}{dt} = \frac{D}{r^* - r} \quad \text{(X)}$$

As before, the degree of hydration α(t) can be expressed as a function of the chemical affinity A(α). α(t) and A(α) satisfy the following equation:

$$\frac{d\alpha}{dt} = \frac{A(\alpha)}{\tau} \quad \text{(XI)}$$

The chemical affinity satisfies the following equation:

$$A(\alpha) = \frac{(1-\alpha)^{2/3}}{(1-\alpha^*)^{1/3} - (1-\alpha)^{1/3}} \quad \text{(XII)}$$

As before, the time characteristic $\tau_x$ associated with reaction of the reactive initial phase X with water can be expressed as a function of the fineness $\Phi$ of the cement, the pressure and the temperature. $\tau_x$ satisfies equation (VI) explained above.

During this second stage, the reference time characteristic $\tau_x(T_0,\Phi_0)$ is controlled by the diffusion of ions through the layer of hydrates around the cement grains (Bernard et al.[12]):

$$\tau_x(T_0, \Phi_0) = \frac{R^2}{3D} \qquad (XIII)$$

The kinetic model 120 used in the method according to the invention advantageously takes into account the effect of the fineness of the cement system, temperature and pressure to simulate the results of evolution of the degree of hydration of the cement system. The activation volume $\Delta V_x$ is advantageously considered to be identical for each of the reactive initial phases. The threshold value of degree of hydration $\alpha^*$ is evaluated by minimizing the difference between $\alpha(t)$, determined according to step A, and $\alpha(t)$ determined experimentally for the cement system, for different temperatures, and at a constant pressure. Advantageously, the pressure is less than or equal to 1 MPa, preferably less than or equal to 0.5 MPa, even more preferably less than or equal to 0.3 MPa. At this low pressure, the effect of the activation volume can in fact be neglected.

According to one embodiment of the invention, the pressure does not affect the threshold degree of hydration $\alpha^*$, which varies only as a function of the temperature. In particular, beyond a certain value of the temperature of hydration, the diffusion phase begins earlier at a higher hydration temperature, and the higher temperature causes increase in the level of C—S—H HD in the long term.

Step C

This step consists of determining the composition of the cement system as a function of time C(t) and as a function of desired values of fineness $\Phi_n$ of the cement system, of pressure $P_n$, and/or of temperature $T_n$, from the degree of hydration $\alpha(t)$ determined in step B.

For this, the method according to the invention uses a composition model 130, which makes it possible to know, at any degree of hydration of the cement system, the system's content of each phase considered. In particular, the volume, mass or mole fraction, preferably volume fraction, of each phase of the cement system is determined.

Firstly, knowledge of $\alpha(t)$, for desired values of fineness of the cement system, of pressure and/or of temperature makes it possible to estimate the fraction, preferably the volume fraction, of the initial phases of the cement system (reactive initial phases of the cement and initial water consumed), as a function of time. Secondly, based on the relations between the molar proportion of the reactants and of the hydrates of the chemical reactions of hydration of the cement system, the fraction, for example volume fraction, of the hydrated phases of the cement system is calculated at a given time. In fact, the chemical equations can be used for determining the proportion as numbers of moles of the reactants and hydrates. The volume fraction is then determined, knowing the density and molecular weight of the hydrates. Thus, the fractions, preferably volume fractions, of the hydrated phases of the cement system, in particular the C—S—H phases and CH phase, are determined. Finally, the fraction, preferably volume fraction, of the aluminates is determined as the difference between the initial proportion, preferably total initial volume, and the calculated proportion, preferably calculated volume, of all the other phases.

Advantageously, the composition model 130 takes into account the temperature at which hydration takes place, notably with regard to determination of the fractions, preferably volume fractions, of the hydrated phases, in particular of the C—S—H phase.

In this step, the composition of the cement system C(t) is determined as a function of time, for desired values of fineness $\Phi_n$ of the cement system, of pressure $P_n$ and/or of temperature $T_n$.

In the method according to the invention, the cement system comprises m phases, including:
- at least one reactive initial phase X, preferably selected from the group consisting of tricalcium silicate $C_3S$, dicalcium silicate $C_2S$, tricalcium aluminate $C_3A$, tetracalcium aluminoferrite $C_4F$, and combinations thereof;
- at least one hydrated phase Y resulting from the hydration of at least one reactive initial phase X, preferably selected from the group consisting of hydrated calcium silicate C—S—H, calcium hydroxide CH, hydrated calcium trisulfoaluminate TSA, hydrated calcium monosulfate AFm, hydrated calcium aluminoferrite, and combinations thereof;
- water;

the initial composition of the cement system $C_0$ comprising a defined initial volume of water $V_w^0$ and at least one reactive initial phase X.

Step C comprises estimation of the composition of the cement system as a function of time C(t) by determining the mole, mass or volume fraction of the m phases of the cement system.

According to one embodiment of the invention:
the volume of at least one reactive initial phase X as a function of time $V_x(t)$ is calculated according to equation (XIV):

$$V_x(t)=V_x^0(1-\alpha_x(t)) \qquad (XIV)$$

with $V_x^0$ the initial volume of the reactive initial phase X, and $\alpha_x(t)$ the degree of hydration of the reactive initial phase X as a function of time;

the volume of at least one hydrated phase as a function of time is calculated according to equation (XV):

$$V(t)=\Sigma V_y^x \cdot \alpha_x(t) \qquad (XV)$$

with $V_y^x$ the volume occupied by the hydrated phase Y formed by the reactive phase X and $\alpha_x(t)$ the degree of hydration of the reactive phase X as a function of time;

the volume of water as a function of time $V_w(t)$ is calculated according to equation (XVI):

$$V_w(t)=V_w^0-\Sigma V_w^x \cdot \alpha_x(t) \qquad (XVI)$$

with $V_w^0$ the initial volume of water in the cement system, $V_w^x$ the volume of water consumed by phase X, $\alpha_x(t)$ the degree of hydration of X as a function of time.

The method according to the invention may moreover take into account other phases, such as incoming water, diffusing from the environment to the pores of the cement system, or at least one gas phase. In this case, the method makes it possible in addition to determine a fraction, for example volume fraction, of water entering the cement system as a function of time, and a fraction, for example volume fraction, of gas as a function of time. For this, the fractions of the incoming water and/or of the gaseous phases are determined on the basis of the phenomenon of chemical shrinkage that occurs during hydration of the cement system.

According to one embodiment of the invention, the volume of the hydrated phase C—S—H is determined as a function of the temperature at which hydration takes place. In particular, the fraction of the phases C—S—H LD and C—S—H HD is determined differently depending on whether hydration takes place at room temperature (20° C.±5° C.), or at a temperature above or below room temperature.

In the case when hydration takes place at room temperature, the fractions, preferably volume fractions, of C—S—H LD and C—S—H HD can be expressed according to the following equations (Bernard et al.[12]):

$$V_{LD}(t)=\Sigma V_{C-S-H}{}^i(\alpha^*-(\alpha^*-\alpha^i(t))\times H[\alpha^*-\alpha^i(t)]) \quad (XVII)$$

$$V_{HD}(t)=\Sigma V_{C-S-H}{}^i(\alpha^i(t)-\alpha^*)\times H[\alpha^i(t)-\alpha^*] \quad (XVIII)$$

where H is the Heaviside function, and i denotes each of the reactions having the hydrated phase as reaction product.

The density of C—S—H HD and C—S—H LD is expressed by:

$$\rho_{HD}=(1-\phi_{HD})\cdot\rho_g+\phi_{HD}\cdot\rho_W \quad (XIX)$$

$$\rho_{LD}=(1-\phi_{LD})\cdot\rho_g+\phi_{LD}\cdot\rho_W \quad (XX)$$

where $\rho_g$ is the density of the globule, preferably equal to 2.65 g/cm³, $\rho_w$ is the density of water, equal to 1 g/cm³, and $\phi_{HD}$ and $\phi_{LD}$ are the respective porosities of C—S—H HD and C—S—H LD.

In the case when hydration takes place at a temperature above room temperature, determination of the composition C(t) takes into account the influence of the temperature, via the temperature-dependent threshold degree of hydration $\alpha^*$, on the fractions of C—S—H LD and C—S—H HD, and optionally on the fraction of incoming water. The fractions, preferably volume fractions, of C—S—H LD and C—S—H HD can be expressed by the same equations (XVII) and (XVIII) above, which take into account a value of the porosity of the C—S—H HD phase different from that at room temperature. The porosity of C—S—H HD at a given temperature is determined by assuming that 1) the amount of globules (of C—S—H LD and of C—S—H HD) only depends on the degree of hydration, 2) the volume of the globules is constant for a given hydration temperature, 3) the density of the globules of C—S—H is barely altered by the temperature, 4) the total porosity is not altered by the temperature and 5) the total pore volume measured by stoving at 105° C. is considered to be the sum of the pore volumes derived from the globules, from C—S—H LD, from C—S—H HD and of the volume of the capillaries.

In fact, in the case of a temperature above room temperature, the volume fraction of C—S—H HD and its density are higher (porosity of C—S—H HD lower) and the volume fraction of C—S—H LD is lower than at room temperature. The macroporosity of the cement system also increases with a higher temperature, for one and the same degree of hydration.

A system of equations (XXI) is thus obtained, for calculating the volume fractions of C—S—H LD and C—S—H HD as well as the porosity of C—S—H HD at a temperature $T_2$ as a function of these same parameters at a temperature $T_1$, provided that the difference in capillary porosity is known.

$$\frac{f_{LD2}}{\alpha_2^*\left(\frac{1-\alpha_2^*}{1-\phi_{HD2}}+\frac{\alpha_2^*}{1-\phi_{LD}}\right)}=\frac{f_{LD1}}{\alpha_1^*\left(\frac{1-\alpha_1^*}{1-\phi_{HD1}}+\frac{\alpha_1^*}{1-\phi_{LD}}\right)} \quad (XXI)$$

$$\frac{f_{HD2}}{(1-\alpha_2^*)\left(\frac{1-\alpha_2^*}{1-\phi_{HD2}}+\frac{\alpha_2^*}{1-\phi_{LD}}\right)}=\frac{f_{HD1}}{(1-\alpha_1^*)\left(\frac{1-\alpha_1^*}{1-\phi_{HD1}}+\frac{\alpha_1^*}{1-\phi_{LD}}\right)}$$

$$f_{LD2}\phi_{LD}+f_{HD2}\phi_{HD2}-f_{LD1}\phi_{LD}-f_{HD1}\phi_{HD1}=\phi_{cp1}-\phi_{cp2}$$

The difference in capillary porosity is for example taken as equal to 6% between the case at a temperature of 60° C. and that at a temperature of 20° C., based on measurements with the mercury porosimeter. Thus, the porosities of C—S—H HD and of C—S—H LD, which are for example 24% and 37% respectively at an ambient temperature of 20° C., are 17% and 37% respectively at a temperature of 60° C.

Step D

This step consists of determining at least one mechanical parameter of the cement system as a function of time, and as a function of the desired values of fineness $\phi_n$ of the cement system, of pressure $P_n$ and/or of temperature $T_n$, from the composition of the cement system C(t) determined in step C.

For this, the method according to the invention uses a method of multi-compositional analysis 140, based on techniques of homogenization such as are used in micromechanics. This method of multi-compositional analysis 140 takes into account a multi-scale model of the cement system for determining, based on homogenization techniques, at least one mechanical parameter of the cement system as a function of time, for a given value of fineness of the cement system, of pressure and/or of temperature, knowing the composition of the cement system C(t) determined in step C, and knowing the evolution of the components of the cement of the cement system obtained from the model of the hydration kinetics used in step A. The multi-scale model comprises at least one elementary scale representing globules of the solid phase C—S—H and a macroscopic scale of the cement system, preferably a multi-scale model comprising three scales.

In this step D, the physicochemical heterogeneity of the cement system, in particular of the hardened cement, is represented by a multi-scale model. A local scale comprises elementary units called globules, representing the solid hydrated phase C—S—H. This local scale represents the smallest scale of the multi-scale model used in this step. A macroscopic scale represents the cement system at the macroscopic scale. Intermediate scales may be used. The bulk modulus $k_s$ and the shear modulus $g_s$ of the globules constitute the two unknowns of the multi-scale model.

Classically, micromechanics, in the mechanics of materials, consists of estimating the mechanical properties of a material by considering a boundary problem of a representative volume element (RVE). According to Zaoui[14], there are three steps for homogenization: description, localization and homogenization.

In the first step, the RVE must be carefully chosen to represent the macroscopic behavior of the material. Thus, to incorporate all the mechanical and geometric information of the heterogeneous phases of the material, the RVE is preferably sufficiently large. Moreover, in the context of continuous media, this volume is preferably sufficiently small to describe the continuity of the macroscopic structure.

In the second step, the interaction of the phases in the RVE is considered. Various well-known homogenization schemes are used. The "diluted" scheme does not consider any interaction between the inclusions in the RVE, and can only be used for low volume fractions of the inclusions. The "Mori-Tanaka" scheme, which takes into account the interaction between the inclusions, is commonly used for a microstructure of composites with a matrix and inclusions. The difference between the "Mori-Tanaka" scheme and the "self-consistent" scheme is that the latter takes the homogenized material as the matrix, solving a system of nonlinear equations for estimating the effective mechanical properties of the material. For the case of a composite material with a matrix and inclusions, the more advanced scheme of "Ponte-Castaneda and Willis" (Pont Castenada et al.[16]) takes into account in addition information on the orientation and spatial distribution of the inclusions in the RVE. After selecting the estimation scheme, the relations between the local stress and strain tensors and the macroscopic stress and strain tensors are established in this step. These relations form a tensor called "strain localization tensor". In cases where the boundary conditions are homogeneous, Hill's lemma[17] provides demonstration that the macroscopic strain and stress are equal respectively to the average of the field of the microscopic strain and stress respectively. For homogeneous linear elastic ellipsoidal inclusions immersed in a homogeneous linear elastic solid medium, Eshelby[18] demonstrated that the strain in the inclusions is homogeneous. Finally, the strain localization tensor is determined as a function of the characteristics of the matrix and of the inclusions.

In the homogenization step, by combining equations of behavior of the material at local and macroscopic level, the elastic and hydro-mechanical coupling parameters can be expressed as a function of the strain localization tensors. For a drained case, the tensor of the rigidity of the material is expressed by:

$$C^{hom} = 3K_d^{hom} J + 2G^{hom} K \quad (XXII)$$

where $$J_{ijkl} = \frac{\delta_{ij}\delta_{kl}}{3};$$

$$K = I - J;$$

$$I = \frac{\delta_{ik}\delta_{jl} + \delta_{il}\delta_{jk}}{2}.$$

$\delta_{ij}$ denotes Kronecker's delta, $K_d^{hom}$ is the drained bulk modulus, $G^{hom}$ is the shear modulus. According to Zaoui[14], for an isotropic case with n spherical inclusions, the effective drained bulk modulus and shear modulus are calculated from the following the expressions (XXIII) and (XXIV):

$$K_d^{hom} = \sum_{r=1}^{n} f_r k_r A_r^v \quad (XXIII)$$

$$G^{hom} = \sum_{r=1}^{n} f_r g_r A_r^d \quad (XXIV)$$

in which $f_r$, $k_r$, and g are respectively the volume fraction, the bulk modulus and the shear modulus of phase r. For the case when all the inclusions are spherical, the volume strain localization tensor $A_v^r$ and the deviatoric strain localization tensor $A_r^d$ are given by the following equations (XXV) and (XXVI):

$$A_r^v = \frac{(1 + \alpha_0(k_r/k_0 - 1))^{-1}}{\sum_r f_r(1 + \alpha_0(k_r/k_0 - 1))^{-1}} \quad (XXV)$$

$$A_r^d = \frac{(1 + \beta_0(g_r/g_0 - 1))^{-1}}{\sum_r f_r(1 + \beta_0(g_r/g_0 - 1))^{-1}} \quad (XXVI)$$

with $$\alpha_0 = \frac{3k_0}{3k_0 + 4g_0}, \beta = \frac{6(k_0 + 2g_0)}{5(3k_0 + 4g_0)},$$

$k_0$ is the bulk modulus of the reference matrix, and $g_0$ is the shear modulus of the reference matrix.

For calculating the rigidity tensor of the solid phase, the Biot coefficient tensor and the homogenized Biot modulus, two cases are considered:

In the first case, the material considered comprises a single porous phase (the pores) and n−1 solid phase. According to Ulm et al.[19], the Biot coefficient tensor of a material having a single porous phase is given by the following equation (XXVII):

$$b^{hom} = 1: \left( I - \sum_{r=1}^{n-1} f_r \langle A \rangle_{V_r} \right) \quad (XXVII)$$

The symbol $\langle A \rangle_V$ denotes the volume mean value of A in the volume V. The homogenized Biot modulus is written in the following form (XXVIII):

$$\frac{1}{N^{hom}} = 1: \sum_{r=1}^{n-1} f_r c_r^{-1} : (1 - 1: \langle A \rangle_{V_r}) \quad (XXVIII)$$

where $c_r$ is the rigidity tensor of phase r, which is defined by the following formula (XXIX):

$$c_r = 3k_r J + 2g_r K \quad (XXIX)$$

In the second case, the material is a multi-scale porous material, for example two scales for simplicity. The generalization with N successive scales is then made without difficulty. The following configuration is taken into account: the material comprises q porous phases (solid and the small pores), a pore volume (large pores) and n−q−1 solid phases. Homogenization consists of performing two steps I and II: the first step II consists of homogenizing q porous phases separately to obtain the effective parameters of each phase of step I ($c_r^I$, $b_r^I$, $N_r^I$, $c_{sr}^I$ which are respectively the rigidity tensor, the Biot coefficient tensor, the Biot modulus, and the rigidity tensor of the solid phase of phase r in step I) as presented in the first case above. The second step II consists of homogenizing q porous phases, a volume of large pores and n−q−1 solid phases. The homogenized Biot tensor in the second step is expressed by the following equation (XXX) (Ulm et al.[19]):

$$b^{hom} = 1 - \sum_{r=1}^{n-1} (f_r \langle A \rangle_{V_r} : (1 - b_r^I))$$  (XXX)

where $b_r$ is Biot's coefficient of phase r. It should be noted that Biot's coefficient of the solid phases is equal to 0. The effective Biot modulus is given by the following expression (XXXI) (Ulm et al.[19]):

$$\frac{1}{N^{hom}} = \sum_{r=1}^{n-1} f_r \left( (c_{sr}^I)^{-1} : (1 - 1 : \langle A \rangle_{V_r}) : (1 - b_r^I) + \frac{1}{N_r^I} \right)$$  (XXXI)

According to one embodiment, the heterogeneity of the cement system in step D is manifested at three scales (Jennings[11]):

An elementary scale Sc.0 in which the globules have a characteristic length of the order of $10^{-9}$ m, and are regarded as representing the solid phase of C—S—H.

A first scale Sc.1 corresponds to the phases C—S—H LD and C—S—H HD, in the form of globules, having a characteristic length between about $10^{-9}$ and $10^{-8}$ m, and further comprises the pores of C—S—H gel.

A second scale Sc.2 corresponds to the cement system having a characteristic length above about $10^{-8}$ m, and comprises the phases C—S—H LD, C—S—H HD, CH, the volume of the capillary pores, the aluminates and the reactive initial phases (the clinker grains).

Within the first scale Sc.1, two inclusions are considered: on the one hand the matrix formed by the solid globules, and on the other hand the pores in the phases C—S—H LD and C—S—H HD. The matrix occupies for example 63% of volume for the case of the C—S—H LD phase, and it occupies for example a proportion above 76%, depending on the temperature, of volume for the C—S—H HD phase. The Mori-Tanaka scheme (Ghabezloo[13]) is selected, with the solid phase playing the role of reference medium. This Mori-Tanaka scheme is appropriate for materials whose solid phase is dominant and for which there are interactions between the particles (Bernard et al.[12]). The effective mechanical parameters, for example the bulk modulus and the shear modulus, of the C—S—H phase, in its two forms C—S—H LD and C—S—H HD, can be determined according to the following equations (XXXII) and (XXXIII), presented in the works of Ghabezloo[13,20].

$$K_X^{hom} = (1 - \phi_X) k_S A_{c,X}^v$$  (XXXII)

$$G_X^{hom} = (1 - \phi_X) g_S A_{c,X}^d$$  (XXXIII)

where X denotes the phase C—S—H LD or the phase C—S—H HD, $k_s$ and $g_s$ are respectively the bulk modulus and the shear modulus of the globules which represent the solid hydrated phase C—S—H at the elementary scale Sc.0 ("s" as solid).

Assuming spherical geometry for all the phases, the strain localization tensors are calculated according to equations (XXV) and (XXVI) described above, with $k_0 = k_s$ and $g_0 = g_s$ ($k_0$ is the bulk modulus of the reference matrix, and $g_0$ is the shear modulus of the reference matrix).

Within the second scale Sc.2, the evolution of the volume fraction of the phases of the cement system during hydration is taken into account. Advantageously, the "self-consistent" scheme is used at this scale. This makes it possible to take into account the percolation threshold, and is appropriate for estimating the elastic properties of the cement system at this scale (Ghabezloo[13]). This second scale Sc.2 comprises six phases: C—S—H LD (LD), C—S—H HD (HD), CH, the volume of the capillary pores (cp), of the aluminates (AL), and the reactive initial phases of the cement, which are for example the clinker grains (CK). At this scale Sc.2, the aluminates phase (solid phase) is assumed to have elastic properties similar to those of C—S—H LD, which are not altered by the hydration temperature. The expressions for the homogenized elastic moduli are as follows:

$$K_{cp}^{hom} = (f_{LD} + f_{AL}) K_{LD}^{hom} A_{LD,cp}^v + f_{HD} K_{HD}^{hom} A_{HD,cp}^v + f_{CH} k_{CH} A_{CH,cp}^v + f_{CK} k_{CK} A_{CK,cp}^v$$  (XXXIV)

$$G_{cp}^{hom} = (f_{LD} + f_{AL}) G_{LD}^{hom} A_{LD,cp}^v + f_{HD} G_{HD}^{hom} A_{HD,cp}^v + f_{CH} g_{CH} A_{CH,cp}^v + f_{CK} g_{CK} A_{ck,cp}^v$$  (xxxv)

The localization tensors are determined from equations (XXV) and (XXVI) described above, with $k_0 = K_{cp}^{hom}$, and $g_0 = G_{cp}^{hom}$ ($k_0$ is the bulk modulus of the reference matrix, and $g_0$ is the shear modulus of the reference matrix).

The parameters at this scale Sc.2 are for example the elastic properties of CH and of the reactive initial phases of the cement (for example the four main components of the clinker).

Computer Program

According to another of its aspects, the invention relates to a software product for storing, in a memory of a unit of a processor or on a removable storage medium suitable for interacting with said unit of the processor, the software product comprising instructions for carrying out the method according to the invention.

EXAMPLES

The invention will be demonstrated with its obvious advantages with the following, nonlimiting example.

The Cement System Cem1

The cement system cem1 given below as an example comprises a Portland cement of class G, with the composition shown in Table 3.

TABLE 3

| Chemical name | Chemical formula | Symbol | Percentage by weight (%) |
|---|---|---|---|
| Tricalcium silicate (alite) | $3CaO \cdot SiO_2$ | $C_3S$ | 55 |
| Dicalcium silicate (belite) | $2CaO \cdot SiO_2$ | $C_2S$ | 18 |
| Tricalcium aluminate | $3CaO \cdot Al_2O_3$ | $C_3A$ | 10 |
| Tetracalcium aluminoferrite (ferrite) | $4CaO \cdot Al_2O_3 Fe_2O_3$ | $C_4AF$ | 8 |
| Calcium sulfate dihydrate (gypsum) | $CaSO_4 \cdot 2H_2O$ | $C\bar{S}H2$ | 6 |

The initial composition $C_0$ of the cement system cem1 is given in Table 4 below. It corresponds to a ratio of water to cement equal to about 044 (w/c).

TABLE 4

| Component | Amount [g] |
|---|---|
| Cement | 914.12 |
| Water | 396.13 |
| Antifoaming agent (D047) | 7.31 |
| Dispersant (D604AM) | 11.06 |
| Anti-sedimentation agent (D153) | 1.37 |

The cement slurry is prepared as follows, by mixing in 5 steps:
mixing distilled water with an antisedimentation agent (D153);
mixing for at least 5 minutes at a speed of about 4200 revolutions per minute;
introducing the other two admixtures: a dispersant and an antifoaming agent (D604AM and D47);
mixing at high speed (a speed of 4200 revolutions per minute) for about 15 seconds while adding cement;
increasing the speed to 12000 revolutions per minute, mixing for 35 seconds.

UCA Test on a Specimen of the Cement System Cem1

The principle of the method and a device of the UCA type are described above and are applied here. After installation of the UCA cell in the system for generating pressure and temperature, the pressure is first increased to the desired value (for example 0.3 MPa, 20 MPa or 40 MPa) and the temperature is then increased to the temperature of the test in 30 min. Measurements of transit time were carried out from the start of the test, at t=0 and T=25° C.

Figure 4:
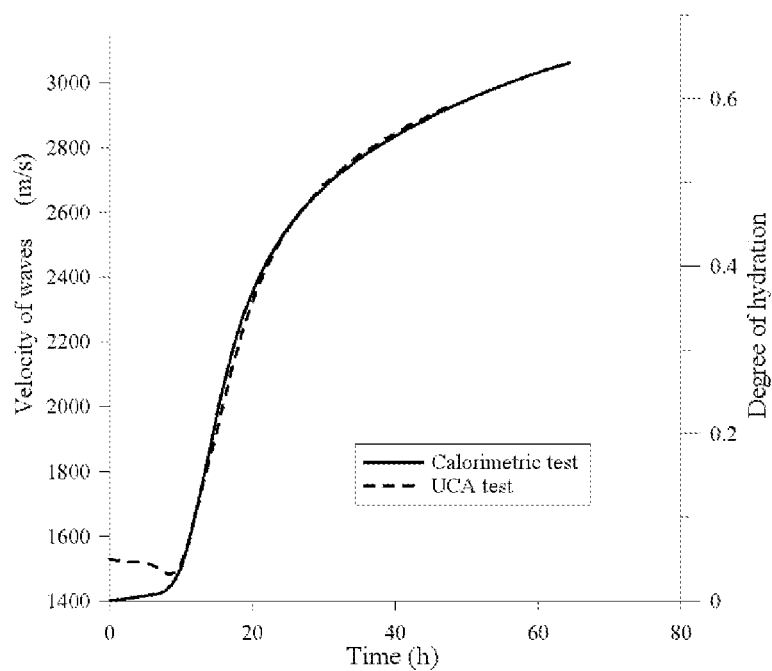
FIG. 4 is a diagram showing the velocity of the compression waves as a function of time $V_p(t)$ measured during a test of the UCA type on a cement system comprising Portland cement, as well as the degree of hydration as a function of time $\alpha(t)$ of the same cement system measured during a calorimetric test.

FIG. 4 shows the velocity of the compression waves as a function of time $V_p(t)$ obtained.

Calorimetric Test on a Specimen of the Cement System Cem1

The principle of a calorimetric test was described above and is applied here. The cement system cem1 is tested by performing an isothermal calorimetric test at 25° C.

FIG. 4 shows the degree of hydration found from this calorimetric test. The curves $\alpha(t)$ and $V_p(t)$ coincide almost completely, which shows that a linear relation exists between the variation over time of the degree of hydration $\alpha(t)$ of the cement system, measured by calorimetry, and the variation over time of the velocity of the compression waves $V_p(t)$.

Figure 5:
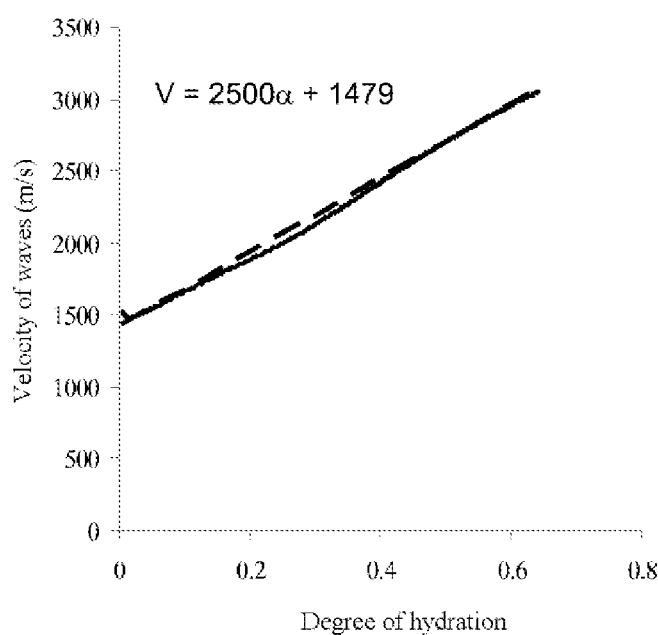
FIG. 5 is a diagram illustrating the linear relation between the velocity of compression waves as a function of time $V_p(t)$ and the degree of hydration as a function of time $\alpha(t)$ as shown in FIG. 3.

FIG. 5 shows that the relation between $\alpha(t)$ and $V_p(t)$ is quasi-linear. The linear regression is expressed thus: $V=2500\alpha+1479$.

Uniaxial Tests on a Specimen of the Cement System Cem1

Uniaxial tests for obtaining measurements of the mechanical parameters, in particular of deformability, are carried out on the system cem1. In order to measure the effect of temperature on the evolution of the elastic properties of the cement system during hydration, cylindrical blocks with a length of 250 mm and a diameter of 100 mm were cured at 20° C. and 60° C. at atmospheric pressure in lime-saturated water. After curing for two days, these blocks were cored and sawn to obtain cylindrical specimens with a length of about 100 mm and a diameter of about 40 mm. These specimens were then stored in a neutral solution (pH=13). Uniaxial tests were carried out at the following ages: 3 days, 4 days, 7 days, 14 days and 35 days. The uniaxial tests were carried out using a press with a capacity of 50 tonnes. The speed of uniaxial displacement used is 0.3 µm/s. Three LVDT sensors (Linear Variable Differential Transformer) were used for measuring the axial strain. Young's modulus is evaluated on the basis of cycles of unloading reloading from 0 MPa to 18 MPa of axial stress.

Steps A and B of the Method: Determination of $\alpha(t)$ at $P_1$, $T_1$, and at Different Values of Fineness $\phi_n$ of the Cement System, of Pressure $P_n$ and of Temperature $T_n$ The velocity of the compression waves as a function of time $V_p(t)$ is measured in a specimen of the cement system cem1, at a pressure $P_1$ and a temperature $T_1$, as described in the UCA test above.

$V\infty$ is determined from the UCA test, and corresponds to 37979 m/s.

Knowing $V_p(t)$ (see FIG. 4), the degree of hydration as a function of time $\alpha(t)$ is determined using the linear relation $\alpha=(V_P-V_0)/(V_\infty-V_0)$.

This degree of hydration as a function of time $\alpha(t)$ is determined for a pressure $P_1$, and a temperature $T_1$, with $P_1$=0.3 or 20 MPa and $T_1$=25° C.

The value of $\tau_x(T_0,\Phi_0)$ used in formula (VI) in the case of the first stage of the hydration process, governed mainly by the phenomena of nucleation and growth, is calculated, using the values of the constants known by a person skilled in the art (Bernard et al.[12]). These values are presented in Table 5. For each reactive initial phase ($C_3S$, $C_2S$, $C_3A$, $C_4AF$), the chemical affinity is calculated using the values from Table 5.

TABLE 5

| Clinker | $\tau_x (T_0, \Phi)$ | $n_x + 1$ | $\alpha_{x0}$ | $\Delta E_x/R$ (° K) |
|---|---|---|---|---|
| $C_3S$ | 13.24 | 1.76 | 0.02 | 4800 |
| $C_2S$ | 72.01 | 1.00 | 0 | 2500 |
| $C_3A$ | 59 | 0.90 | 0.04 | 5500 |
| $C_4AF$ | 24.68 | 2.34 | 0.4 | 4200 |

The value of $\tau_x(T_0,\Phi_0)$ used in formula (VI) in the case of the second stage of the process of hydration of the cement system, governed mainly by the phenomenon of diffusion (period of curing in the case of cem1), is calculated from the values given in the following Table 6:

TABLE 6

| Clinker | $C_3S$ | $C_2S$ | $C_3A$ | $C_4AF$ |
|---|---|---|---|---|
| $\tau_x$ (h) | 3492 | 564939 | 1439 | 3433 |

The value of the threshold degree of hydration $\alpha^*$ for the cement system cem1 is given in Table 7 below. $\alpha^*$ is evaluated by minimizing the difference between the curves determined on the basis of the method according to the invention and the experimental curves for different temperatures at 0.3 MPa because, for this low pressure, the effect of the variable $\Delta V$ expressed in formula (VI) can be neglected.

TABLE 7

| T (° C.) | 7 | 13 | 15 | 25 | 30 | | 40 | | 60 | |
|---|---|---|---|---|---|---|---|---|---|---|
| Pressure (MPa) | 0.3 | 0.3 | 40 | 0.3 | 20 | 40 | 0.3 | 40 | 0.3 | 20 |
| α* | 0.68 | 0.70 | 0.68 | 0.72 | 0.72 | 0.72 | 0.60 | 0.60 | 0.40 | 0.40 |

Figure 6:
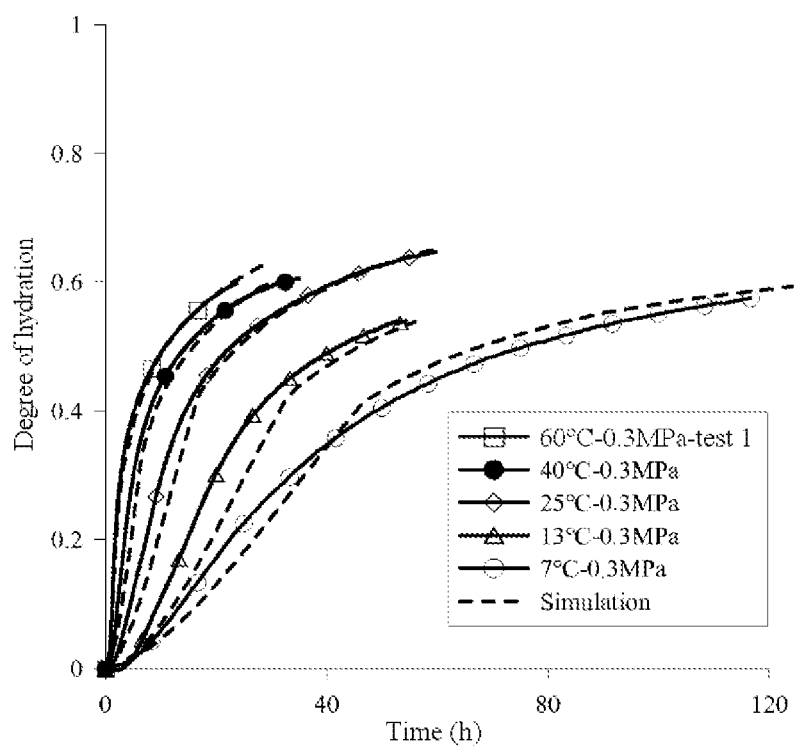
FIGS. 6 to 8 are diagrams comparing the degree of hydration as a function of time α(t) determined by the method according to the invention for a given cement system, and the degree of hydration as a function of time α(t) for this same system, determined experimentally. The degrees of hydration are shown for different values of pressure and temperature.
Figure 7:
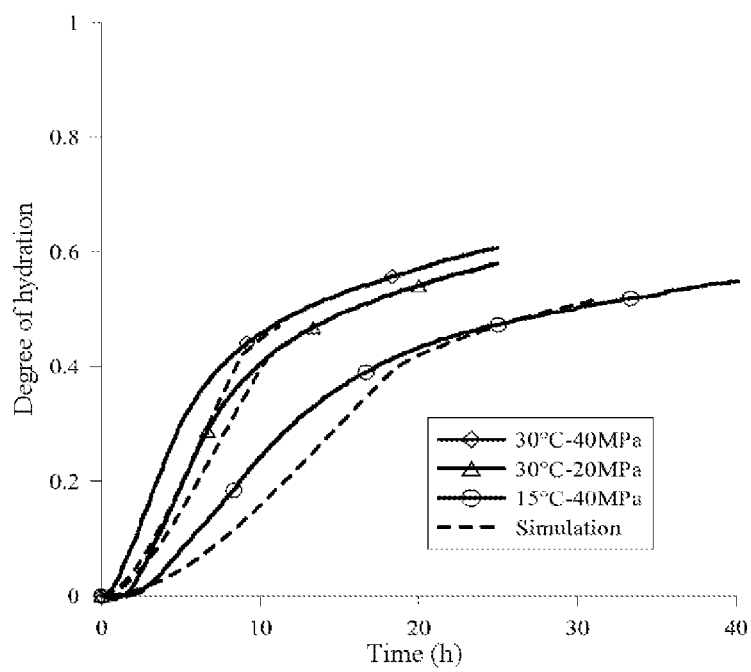
Figure 8:
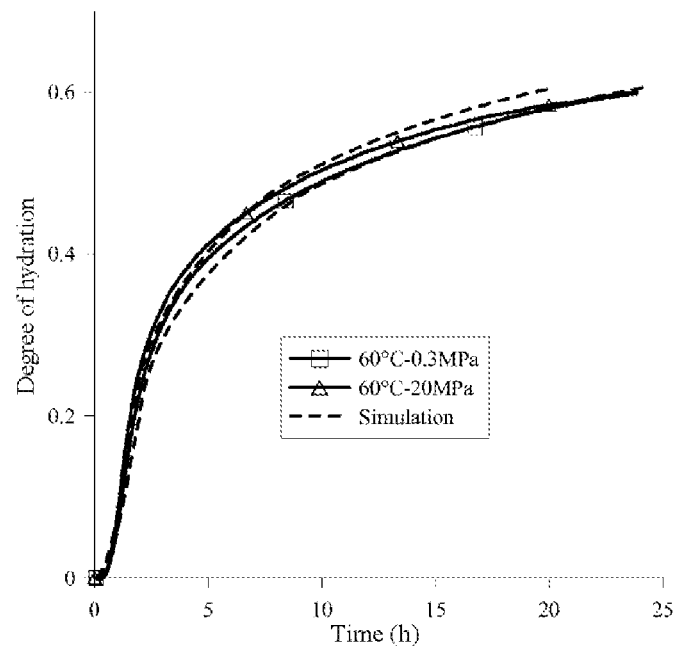

FIGS. 6 to 8, which compare experimental data obtained from UCA tests as described above, and the data obtained from determination of the degree of hydration according to steps A and B of the method of the invention (curves with dashed lines, indicated as "simulation" in the legend), show the good predictive capacity of steps A and B of the method of the invention.

Step C of the Method: Determination of the Composition C(t)

In this step, stages 1 and 2 of the hydration process, comprising the phases of initial and dormant hydration, are not taken into account. Stages 3 and 4, comprising the phases of acceleration and slowing of hydration, are taken into account and simulated according to Avrami's theory of nucleation and growth[3]. Stage 5 comprising the curing phase is also taken into account, and is considered to be controlled by diffusion phenomena.

Figure 9:
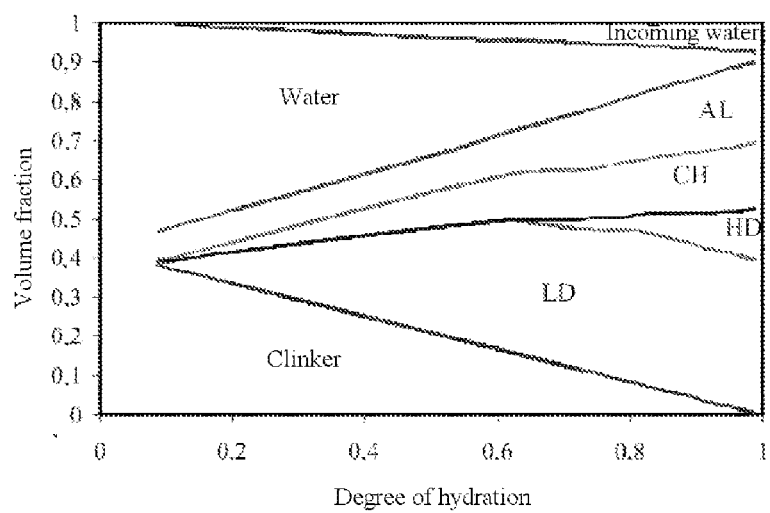
FIG. 9 is a diagram illustrating the composition of a given cement system as a function of the degree of hydration of the system, determined by the method according to the invention. In particular, the volume fraction of the various constituents of the cement system is given as a function of the degree of hydration of the cement system, for a fixed pressure/temperature pair.

FIG. 9 shows the variation of the volume fractions of the different phases of the cement system cem1 as a function of the degree of hydration, for a hydration temperature of 20° C. and at atmospheric pressure.

Step D of the Method

Table 8 presents the bulk moduli k and shear modulus g of the different solid components taken into account during the multi-scale analysis, according to step D of the method: the four phases of the clinker of system cem1, the hydrated phase CH and the globules representing the solid phase C—S—H of the cement system cem1. All these values were obtained from the literature, except with regard to the moduli of the globules, which were obtained by calibration with the data from tests carried out by Bourissai[21].

The multi-scale analysis includes two homogenizations:
the first homogenization considers on the one hand the matrix formed by the solid globules of C—S—H, and on the other hand the pores in phases C—S—H LD and C—S—H HD. It makes it possible to calculate the bulk modulus and shear modulus of the "porous" C—S—H LD and C—S—H HD. The characteristic length is about $10^{-9}$-$10^{-8}$ m. The matrix occupies 63% of volume for the case of the C—S—H LD phase, and it occupies a proportion above 76%, depending on the temperature, of volume for the C—S—H HD phase;
the second homogenization considers on the one hand the solid phases (C—S—H LD, C—S—H HD, CH, aluminates and reactive initial phases of the clinker) and on the other hand the capillary porosity. It makes it possible to calculate the bulk modulus and shear modulus of the cement system and then all of the elastic and hydro-mechanical parameters. The characteristic length is about $10^{-8}$ m.

TABLE 8

| | $C_3S$ | $C_2S$ | $C_3A$ | $C_4AF$ | CH | C-S-H globule |
|---|---|---|---|---|---|---|
| k[GPa] | 112.5 | 116.7 | 120.8 | 104.2 | 32.5 | 23.0 |
| g[GP] | 51.9 | 53.8 | 55.8 | 48.1 | 14.6 | 17.0 |

FIGS. 10 to 13 show good correspondence between the mechanical parameters determined according to the method of the invention, and the experimental data obtained in the literature (Boumiz et al.[1]; Haecker et al.[2]), thus validating the method according to the invention. The data from the literature were corrected, in order to transform the dynamic moduli into static moduli, using the following formula:

$$E_{static} = 0.83 \times E_{dynamic}$$

Figure 10:
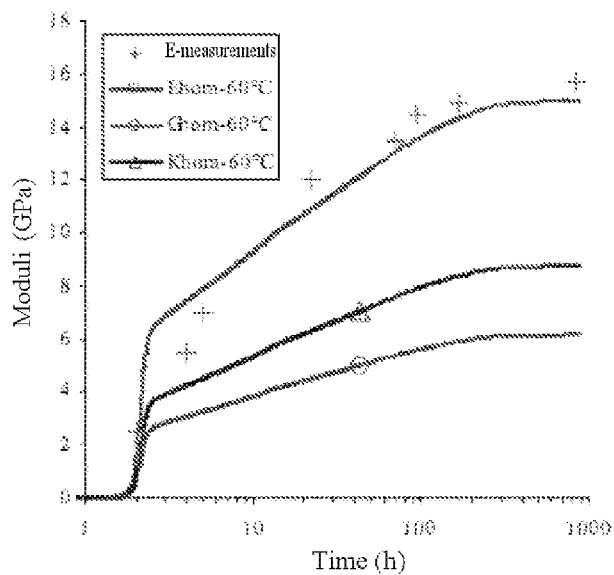
FIGS. 10 to 13 are diagrams comparing the mechanical parameters as a function of time determined by the method according to the invention, for a given cement system, with those determined experimentally and obtained from the literature (Boumiz et al.[1], Haecher et al.[2]) for this same cement system.

FIG. 10, for example, compares the measured data ("E-Measurements" in the legend, symbols in the form of crosses) and the data determined by the method according to the invention for the Young's modulus (E), for a curing temperature of 60° C. ("Ehom" in the legend). The bulk modulus (K) and shear modulus (G) determined by the method according to the invention are also shown ("Khom" and "Ghom" in the legend). The shear modulus of the cement paste hydrated at 60° C., at age of 1000 h (42 days) is 6.1 GPa. The difference between this value and the measured value (5.9 GPa) is 3.3%.

Figure 11:
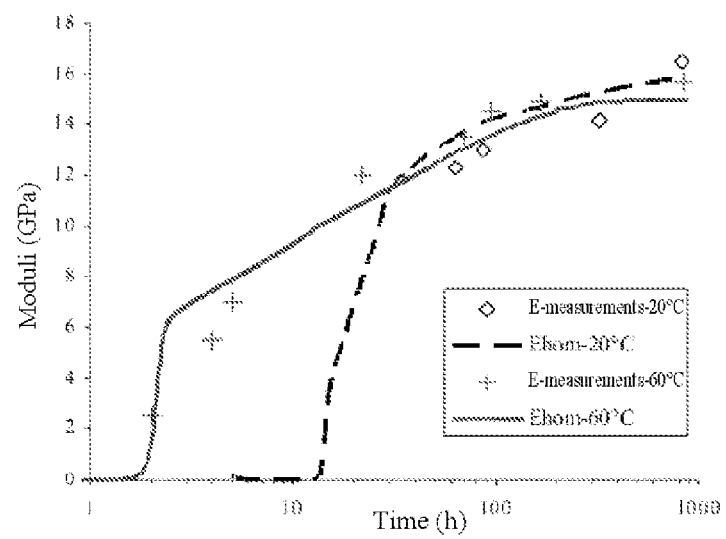

FIG. 11 also shows good correspondence between the experimental data (shown as cross and diamond symbols, and indicated as "E-measurements" in the legend) and the mechanical parameters determined according to the invention (solid and dashed curves, and indicated as "Ehom" in the legend). This figure also shows the effect of the hydration temperature on the variation of the elastic properties of the cement system: the long-term value of Young's modulus is greater for hydration at 20° C. than at 60° C.

Figure 12:
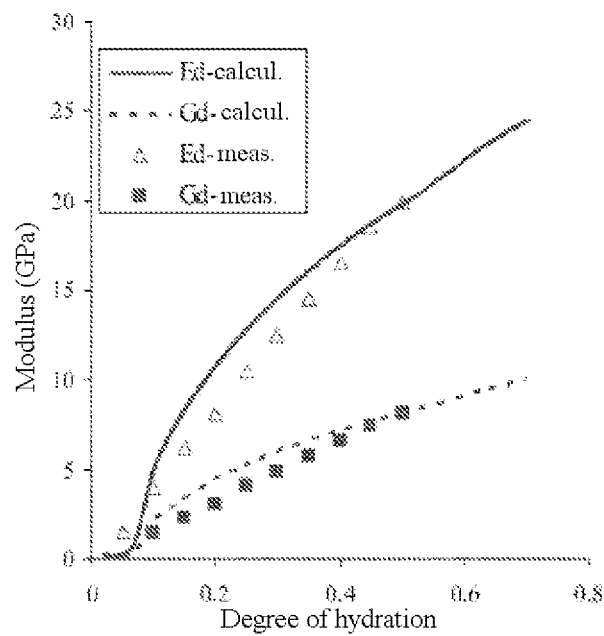

FIG. 12 shows very good correspondence between the measured data (shown with square and triangle symbols, and indicated as "Ed/Gd-measurements" in the legend) and data predicted according to the invention (solid and dashed curves, and indicated as "Ed/Gd-calculation" in the legend), both for the Young's modulus and for the shear modulus.

Figure 13:
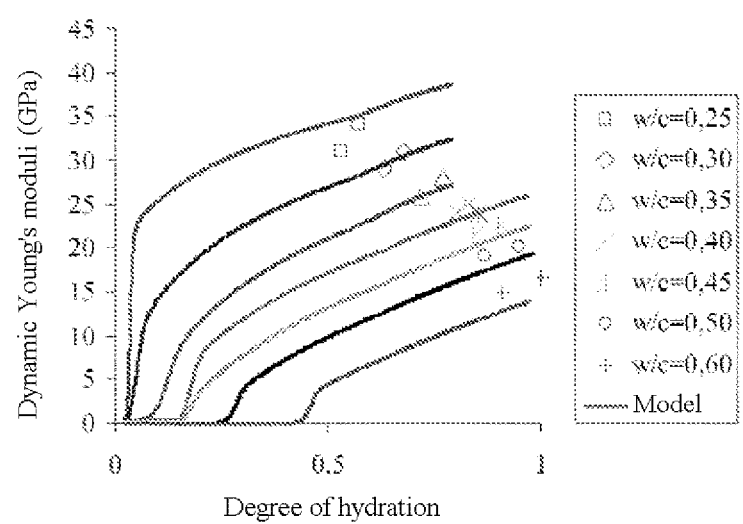

FIG. 13 also shows good correspondence between the experimental data (shown with various symbols) and the mechanical parameters determined according to the invention (solid curves). This figure also shows the effect of the ratio of water to cement on the evolution of the elastic properties of the cement system: the long-term value of Young's modulus is greater for a low ratio of water to cement.

LIST OF BIBLIOGRAPHIC REFERENCES CITED IN THE DESCRIPTION (1) Boumiz A., Veet C., Cohen Tenoudjit F., "Mechanical properties of cement pastes and mortars at early ages", Advanced Cement based materials, 3, p.94-106 (1996).
(2) Haecker C. J., Garboczi E. J., Bohn J. W., Sun Z., Shah S. P., Voigt T., "Modeling the linear elastic properties of Portland cement paste", Cement concrete research, 35, p. 1948-1960 (2005).
(3) Avrami, M., "Kinetics of phase change, Journal of Chemical Physics", 7, p. 1103-1124, 9, p.177-184 (1939-1940).
(4) Kondo R., Kodama, M., "On the hydration kinetics of cement, Semento Gijutsu Nenpo", 21, p. 77-828 (1967).

(5) Fuji, K., Kondo, W., "Kinetics of the hydration of tricalcium silicate", Journal of the American Ceramic Society, 57 (11), p. 492-497 (1974).

(6) Jennings H. M., Tennis P. D., "Model for the developing microstructure in Portland Cement Pastes", J. Am. Ceram. Soc., 77 (12), p. 3161-3172 (1994).

(7) Reddy, B. R., Santra, A., McMechan, D., Gray, D., Brenneis, C., Dunn, R., "Cement mechanical property measurements under wellbore conditions", SPE 95921 (2005).

(8) Jennings H. M., 'A model for the microstructure of calcium silicate hydrate in cement paste', Cement and Concrete Research, 30, p. 101-116 (2000).

(9) Jennings H. M., "Colloid model of C—S—H and implications to the problem of creep and shrinkage", Materials and Structures/Concrete Science and Engineering, 37, p. 59-70 (2004).

(10) Constantinides G., "Invariant mechanical properties of Calcium-Silicate-Hydrates (CS—H) in Cement-Based materials: instrumented nanoindentation and microporomechanical modelling", PhD thesis, Massachusetts institute of Technology (2006).

(11) Jennings H. M., "Refinements to colloid model of C—S—H in cement: CM-II", Cement and Concrete Research, 38, p. 275-289 (2008).

(12) Bernard, O., Ulm, F.-J., Lemarchand, E. "A multiscale micromechanics-hydration model for the early-age elastic properties of cement-based materials", Cement and Concrete Research, 33, p. 1293-1309 (2003).

(13) Ghabezloo S., "Association of macroscopic laboratory testing and micromechanics modelling for the evaluation of the poroelastic parameters of a hardened cement paste", Cement and Concrete research, 40 (8), p. 1197-1210 (2010).

(14) Zaoui A., "Continuum micromechanics: survey", Journal of Engineering Mechanics, 128 (8), p. 808-816 (2002).

(15) Rixom, R., Mailvaganam, N. "Chemical admixtures for concrete", Third edition, Spons Architecture Price Book, 456 p. (1999).

(16) Pont Castenada, P., Willis, R. "The effect of spatial distribution on the effective behaviour of composite materials and cracked media", J. Mech. Phys. Solids, 43, p. 1919-1951 (1995).

(17) Hill, R. "The essential structure of constitutive laws for metal composites and polycrystals", J. Mech. Phys. Solids, 15, p. 79-95. (1967).

(18) Eshelby, J. D. "The determination of the elastic field of an ellipsoidal inclusion", Proceedings of the Royal Society of London, 241, p. 376-392 (1957).

(19) Ulm, F.-J., Constantinides, G., Heukamp, F. H. "Is concrete a poromechanics material?—A multiscale investigation of poroelastic properties", Materials and Structures, 37 (265), p. 43-58 (2004).

(20) Ghabezloo S., "Micromechanics analysis of thermal expansion and thermal pressurization of a hardened cement paste", Cement and Concrete research, 41 (5), p. 520-532 (2011).

(21) Bourissai, M. "Thermal, chemical and hydro-mechanical behavior of an oil-industry cement at very young age in HP/HT setting conditions. Experimental approach and analysis by change of scale", Doctorate Thesis, Université Paris Est, 246 p. (2010).

The invention claimed is:

1. A method for determining mechanical parameters of a cement system of initial composition $C_0$ and of fineness $\Phi$, as a function of time, and as a function of fineness of the cement system, pressure and temperature, comprising the following steps:

(A) determining a degree of hydration of the cement system as a function of time $\alpha(t)$ from a velocity of a compression waves as a function of time $V_p(t)$ measured in a specimen of the cement system, at a pressure $P_1$ and a temperature $T_1$;

(B) determining the degree of hydration $\alpha(t)$ as a function of desired values of fineness $\Phi_n$ of the cement system, of pressure $P_n$ and of temperature $T_n$;

(C) determining a composition of the cement system as a function of time $C(t)$ and as a function of desired values of fineness $\Phi_n$ of the cement system, of pressure $P_n$ and of temperature $T_n$, from the degree of hydration $\alpha(t)$ determined in step B;

(D) determining at least one mechanical parameter of the cement system as a function of time, and as a function of the desired values of fineness $\Phi_n$ of the cement system, of pressure $P_n$ and of temperature $T_n$, from the composition of the cement system $C(t)$ determined in step C.

2. The method as claimed in claim 1, further comprising an initial step of measurement of the velocity of the compression waves as a function of time $V_p(t)$ in a specimen of the cement system.

3. The method as claimed in claim 1, wherein said mechanical parameter is selected from static deformability parameters.

4. The method as claimed in claim 3, wherein static deformability parameters are two static elastic parameters selected from static Young's modulus E, static Poisson's ratio $\Box$, bulk modulus K, shear modulus G.

5. The method as claimed in claim 3, further comprising determination of a mechanical parameter selected from the parameters of hydro-mechanical coupling.

6. The method as claimed in claim 1, wherein the degree of hydration of the cement system as a function of time $\alpha(t)$ is calculated from $V_p(t)$ according to a linear relation.

7. The method as claimed in claim 6, wherein the degree of hydration of the cement system as a function of time $\alpha(t)$ is calculated from $V_p(t)$ according to the relation $\alpha=(V_p-V_0)/(V_\infty-V_0)$, with $V_0$ and $V_P$ corresponding respectively to the velocity of the compression waves measured in the specimen of the cement system at time t=0 and at time t, and $V_\infty$ corresponding to the velocity of the compression waves in a specimen of a fully hydrated cement system.

8. The method as claimed in claim 1, wherein the hydration process comprises a first stage in which hydration is mainly governed by a process of nucleation and growth, and a second stage in which hydration is mainly governed by an ion diffusion process, said second stage starting when the degree of hydration $\alpha$ reaches a threshold value degree of hydration $\alpha^*$, this threshold value $\alpha^*$ being a function of the temperature, and in which step B comprises the following substeps:

(B-i) determination of the degree of hydration $\alpha(t)$ during the first stage of the process of hydration of the cement system;

(B-ii) determination of the degree of hydration $\alpha(t)$ during the second stage of the process of hydration of the cement system;

each of the substeps B-i and B-ii taking into account the fineness $\Phi$ of the cement system, the pressure and the temperature for determining the degree of hydration $\alpha(t)$.

9. The method as claimed in claim 8, wherein the threshold value of degree of hydration $\alpha^*$ is evaluated by minimizing the difference between $\alpha(t)$ determined using a kinetic model 120 and $\alpha(t)$ determined experimentally from the velocity of the compression waves, for different temperatures, and at a constant pressure, so as to take into account a variation of $\alpha^*$ as a function of the temperature in step B.

10. The method as claimed in claim 9, wherein:
the cement system of initial composition $C_0$ comprises a cement and water, the cement comprising at least one reactive initial phase X;
the degree of hydration $\alpha(t)$ determined in step B corresponds to a weighted average of the degrees of hydration of each of the reactive initial phases X of the cement;
the degree of hydration of each of the reactive initial phases X of the cement is a function of a ratio of a chemical affinity $A_x(\alpha)$ of the reactive initial phase X, this chemical affinity $A^x(\alpha)$ controlling a rate of variation of the hydration of the reactive initial phase X, to a characteristic time associated with reaction of the reactive initial phase X with water $\tau_x$;
and the characteristic time associated with reaction of the reactive initial phase X with water is $\tau_x$ is a function of the fineness $\Phi$ of the cement, the pressure and the temperature.

11. The method as claimed in claim 10, wherein the characteristic time associated with reaction of the reactive initial phase X with water $\tau_x$ is expressed according to the following equation:

$$\tau_x(T, \Phi) + \sqrt[n_x+1]{\frac{\Phi_0}{\Phi}} \times \tau_x(T_0, \Phi_0) \exp\left(\frac{\Delta E_x}{R}\left(\frac{1}{T} - \frac{1}{T_0}\right) + \frac{\Delta V_x}{R}\left(\frac{P}{T} - \frac{P_0}{T_0}\right)\right) \quad (VI)$$

where $\Phi_0$ is the fineness of a reference cement, $T_0$ is a initial temperature and $P_0$ is a initial pressure at time $t=0$ of the hydration process, R is a gas constant, $\Delta E_x$ is an activation energy, $\Delta V_x$ is an activation volume for nucleation and growth of the hydrates during the first stage of the hydration process and $n_x$ is a constant.

12. The method as claimed in claim 1, wherein the cement system comprises m phases, including:
at least one reactive initial phase X;
at least one hydrated phase Y resulting from the hydration of at least one reactive initial phase X;
water;
the initial composition of the cement system $C_0$ comprising a defined initial volume of water $V_w^0$ and at least one reactive initial phase X,
and in which step C comprises estimation of the composition of the cement system as a function of time $C(t)$ by determining a mole, mass or volume fraction of the m phases of the cement system.

13. The method as claimed in claim 12, wherein:
the volume of at least one reactive initial phase X as a function of time $V_x(t)$ is calculated according to equation (XIV):

$$V_x(t) = V_x^0(1 - \alpha_x(t)) \quad (XIV)$$

with $V_x^0$ the initial volume of the reactive initial phase X, and $\alpha_x(t)$ the degree of hydration of the reactive initial phase X as a function of time;
the volume of at least one hydrated phase as a function of time is calculated according to equation (XV):

$$V(t) = \Sigma V_y^x \cdot \alpha_x(t) \quad (XV)$$

where $V_y^x$ is the volume occupied by the hydrated phase Y formed by the reactive phase X in a representative volume element, and $\alpha_x(t)$ is the degree of hydration of the reactive phase X as a function of time;
the volume of water as a function of time $V_w(t)$ is calculated according to equation (XVI):

$$V_w(t) = V_w^0 - \Sigma V_w^x \cdot \alpha_x(t) \quad (XVI)$$

where $V_w^0$ is the initial volume of water in the cement system, $V_w^x$ is the volume of water consumed by phase X, $\alpha_x(t)$ is the degree of hydration of X as a function of time.

14. The method as claimed in claim 1, wherein step D is carried out according to a method of multi-compositional analysis (140), said method of multi-compositional analysis (140):
taking into account a multi-scale model of the cement system, said multi-scale model comprising at least one elementary scale representing globules of a solid phase C—S—H and a macroscopic scale of the cement system;
and allowing determination of at least one mechanical parameter of the cement system as a function of time, for a given value of fineness of the cement system, of pressure and/or of temperature, using homogenization techniques, knowing the composition of the cement system C(t) determined in step C, and knowing an evolution of the components of the cement of the cement system obtained from the model of the hydration kinetics used in step A.

15. The method as claimed in claim 1, wherein the cement system comprises Portland cement.

16. The method as claimed in claim 1, for characterizing the mechanical behavior of a cement system used as cement sheath or plug in a well.

17. A software product for storing, in a memory of a unit of a processor or on a removable storage medium suitable for interacting with said processor unit, the software product comprising instructions for carrying out the method as claimed in claim 1.

18. The method of claim 3, wherein the static deformability parameters are static elastic parameters selected from static Young's modulus E, static Poisson's ratio $\nu$, bulk modulus K, shear modulus G, and combinations thereof.

19. The method of claim 11, wherein the fineness of a reference cement $\Phi 0$ is 3600 cm$^2$/g.

20. The method of claim 12, wherein the at least one reactive initial phase X is selected from the group consisting of tricalcium silicate C3S, dicalcium silicate C2S, tricalcium aluminate C3A, tetracalcium aluminoferrite C4F, and combinations thereof, and the least one hydrated phase Y resulting from the hydration of at least one reactive initial phase X is selected from the group consisting of hydrated calcium silicate C—S—H, calcium hydroxide CH, hydrated calcium trisulfoaluminate TSA, hydrated calcium monosulfate AFm, hydrated calcium aluminoferrite, and combinations thereof.

* * * * *